(12) United States Patent
Hollands et al.

(10) Patent No.: US 10,344,078 B2
(45) Date of Patent: Jul. 9, 2019

(54) TYPE III SECRETION SYSTEM TARGETING MOLECULES

(71) Applicant: Inhibrx, Inc., La Jolla, CA (US)

(72) Inventors: Andrew Hollands, La Jolla, CA (US); John C. Timmer, La Jolla, CA (US); Quinn Deveraux, La Jolla, CA (US); Brendan P. Eckelman, La Jolla, CA (US)

(73) Assignee: Inhibrx, Inc., La Jolla, CA (US)

( * ) Notice: Subject to any disclaimer, the term of this patent is extended or adjusted under 35 U.S.C. 154(b) by 0 days.

(21) Appl. No.: 15/144,470

(22) Filed: May 2, 2016

(65) Prior Publication Data
US 2016/0318996 A1    Nov. 3, 2016

Related U.S. Application Data

(60) Provisional application No. 62/155,967, filed on May 1, 2015, provisional application No. 62/254,992, filed on Nov. 13, 2015.

(51) Int. Cl.
*C07K 14/21* (2006.01)
*C07K 16/12* (2006.01)
*A61K 38/00* (2006.01)

(52) U.S. Cl.
CPC ......... *C07K 16/1214* (2013.01); *C07K 14/21* (2013.01); *A61K 38/00* (2013.01); *C07K 2317/31* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 2009/0191186 | A1* | 7/2009 | Bebbington | C07K 16/1214 424/130.1 |
| 2011/0165172 | A1 | 7/2011 | Yarranton | |
| 2012/0064106 | A1* | 3/2012 | Mizel | A61K 39/104 424/192.1 |
| 2013/0266575 | A1* | 10/2013 | Klade | A61K 39/104 424/139.1 |
| 2015/0284450 | A1 | 10/2015 | Digiandomenico et al. | |

FOREIGN PATENT DOCUMENTS

| | | |
|---|---|---|
| JP | 2008133206 A * | 6/2008 |
| WO | WO 2006/073941 A2 | 7/2006 |
| WO | WO 2013/070565 A1 | 5/2013 |
| WO | 2013070615 | 6/2013 |
| WO | WO 2013128031 A1 * | 9/2013 ......... C07K 16/1214 |
| WO | 2014074528 A3 | 7/2014 |

OTHER PUBLICATIONS

Saerens et al. 2008 (Single-domain antibodies as building blocks for novel therapeutics; Current Opinion in Pharmacology 8:600-608) (Year: 2008).*
Greenspan et al. 1999 (Defining epitopes: It's not as easy as it seems; Nature Biotechnology, 17:936-937). (Year: 1999).*
Rudikoff et al. 1982 (Single amino acid substitution altering antigen-binding specificity; PNAS, USA, 79(6):1979-1983) (Year: 1982).*
Sela-Culang et al. 2013 (the structural basis of antibody-antigen recognition; Frontiers in Immunology 4(302):1-13) (Year: 2013).*
Alegre et al. "Effect of a single amino acid mutation on the activating and immunosuppressive properties of a 'humanized' OKT3 monoclonal antibody", The Journal of Immunology, 1992, vol. 148, p. 3461-3468.
Baldrick P. "Pharmaceutical Excipient Development: The Need for Preclinical Guidance" Regulatory Toxicology and Pharmacology, 2000, vol. 32, p. 210-218.
Bowie et al. "A Method to Identify Protein Sequences That Fold into a Known Three-Dimensional Stucture", 1991, Science, vol. 253, p. 164-171.
Carter, "Bispecific human IgG by design", Journal of Immunological Methods, 2001, vol. 248, p. 7-15.
Charman W. "Lipids, Lipophilic Drugs, and Oral Drug Delivery—Some Emerging Concepts" Journal of Pharmaceutical Sciences, 2000, vol. 89, No. 8, p. 967-978.
Chothia & Lesk "Canonical Structures for the Hypervariable Regions of Immunoglobulins", J. Mol. Biol., 1987, vol. 196, p. 901-917.
Chothia et al. "Conformations of immunoglobulin hypervariable regions", Nature, 1989, vol. 342, p. 877-883.
Dall' Acqua et al. "Properties of Human IgG1s Engineered for Enhanced Binding to the Neonatal Fc Receptor (FcRn)", The Journal of Biological Chemistry, 2006, vol. 281, No. 32, p. 23514-23524.
Davies et al. "Antibody-Antigen Complexes", Annual Rev Biochem, 1990, vol. 59, p. 439-473.
DiGiandomenico, et al. "A multifunctional bispecific antibody protects against *Pseudomonas aeruginosa*", Science Translation Medicine, 2014, vol. 6, Issue 262, p. 13 pages, 262ra155.
Evans et al. "Design of Nonpeptidal Ligands for a Peptide Receptor: Cholecystokinin Antagonists", J. Med. Chem., 1987, vol. 30, p. 1229-1239.
Fauchere, "Elements for the Rational Design of Peptide Drugs", Advances in Drug Research, 1986, vol. 15, p. 29-69.
Idusogie et al. "Engineered Antibodies with Increased Activity to Recruit Complement", The Journal of Immunology, 2001, vol. 166, No. 4, p. 2571-2575.
Kaneko and Niwa, "Optimizing Therapeutic Antibody Function", Biodrugs, 2011, vol. 25, No. 1, p. 1-11.

(Continued)

*Primary Examiner* — Mary Maille Lyons
(74) *Attorney, Agent, or Firm* — McNeill Baur PLLC

(57) ABSTRACT

This invention relates generally to molecules that specifically bind bacterial V-tip proteins of the type III secretion system of Gram negative bacteria such as PcrV from *Pseudomonas aeruginosa*. More specifically, this invention relates to molecules that block the injection of effector molecules into target cells. This invention also relates to molecules that specifically bind to bacterial lipoproteins, such as OprI. The molecules of the present invention are monospecific or multispecific and can bind their target antigen in a monovalent or multivalent manner. The invention also relates generally to molecules that specifically bind bacterial cell surface proteins such as OprI, and to methods of use these molecules in a variety of therapeutic, diagnostic, and/or prophylactic indications.

19 Claims, 7 Drawing Sheets
Specification includes a Sequence Listing.

(56) References Cited

OTHER PUBLICATIONS

Lazar et al. "Engineered antibody Fc variants with enhanced effector function", PNAS, 2006, vol. 103, No. 11, p. 4005-4010.

Malmqvist, M. "Biospecific interaction analysis using biosensor technology", Nature, 1993, vol. 361, p. 186-187.

Moore et al., "Engineered Fc variant antibodies with enhanced ability to recruit complement and mediate effector function", mAbs, 2010, vol. 2, No. 2, p. 181-189.

Natsume et al. "Engineered Antibodies of IgG1/IgG3 Mixed Isotype with Enhanced Cytotoxic Activities", Cancer Research, 2008, vol. 68, No. 10, p. 3863-3872.

Powell et al. "Compendium of Excipients for Parenteral Formulations" PDA Journal of Pharmaceutical Science and Technology, 1998, vol. 52, p. 238-311.

Rizo and Gierasch "Constrained Peptides: Models of Bioactive Peptides and Protein Substructures", Ann. Rev. Biochem. 1992, vol. 61, p. 387-418.

Shields et al. "High Resolution Mapping of the Binding Site on Human IgG1 for FcγRI, FcγRII, FcγRIII, and FcRn and Design of IgG1 Variants with Improved Binding to the FcγR", The Journal of Biological Chemistry, 2001, vol. 276, No. 9, p. 6591-6604.

Stavenhagen et al. "Fc Optimization of Therapeutic Antibodies Enhances Their Ability to Kill Tumor Cells In vitro and Controls Tumor Expansion In vivo via Low-Affinity Activating Fcγ Receptors", Cancer Research, 2007, vol. 67, No. 18, p. 8882-8890.

Stavenhagen et al. "Enhancing the potency of therapeutic monoclonal antibodies via Fc optimization", Advances in Enzyme Regulations, 2008, vol. 48, p. 152-164.

Thornton et al. "Prediction of progress at last", Nature, 1991, vol. 354, p. 105-106.

Veber and Freidinger "The design of metabolically-stable peptide analogs", TINS, Sep. 1985, p. 392-396.

Wang W. "Lyophilization and development of solid protein pharmaceuticals." International Journal of Pharmaceutics, 2000, vol. 203, Nos. 1-2, p. 1-60.

Zalevsky et al. "Enhanced antibody half-life improves in vivo activity", Nature Biotechnology, 2010, vol. 28, No. 2, p. 157-159.

Extended European Search Report for EP16789896.4 dated Sep. 26, 2018, 9 pages.

Rahner et al., "Protektion immunsupprimierter Mause gegen Pseudomonas aeruginosa durch monoklonale Antikorper gegen ausseres Membranprotein I (Opr I)", Infection, vol. 18, No. 4, pp. 242-245, Jul. 1, 1990.

Sato, Hiromi et al., "Modified Needle-Tip PcrV Proteins Reveal Distinct Phenotypes Relevant to the Control of Type III Secretion and Intoxication by Pseudomonas Aeruginosa," PLOS One, vol. 6, No. 3, p. e18356, Mar. 29, 2011.

* cited by examiner

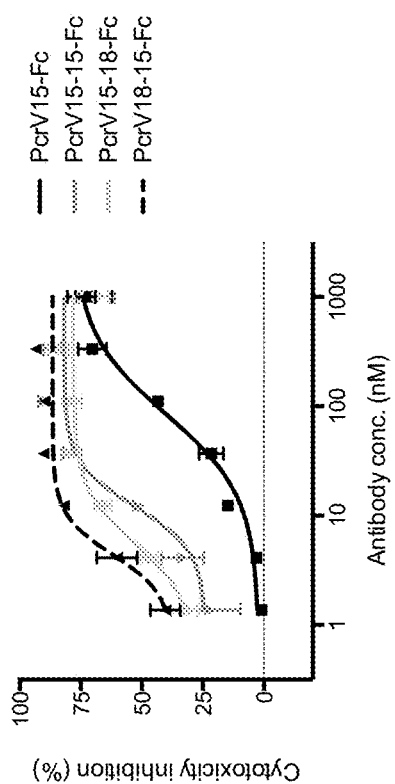
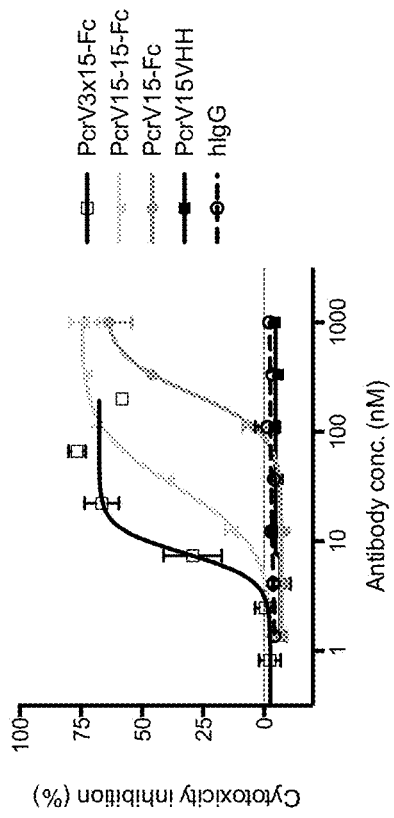
Figure 3A
Figure 3B

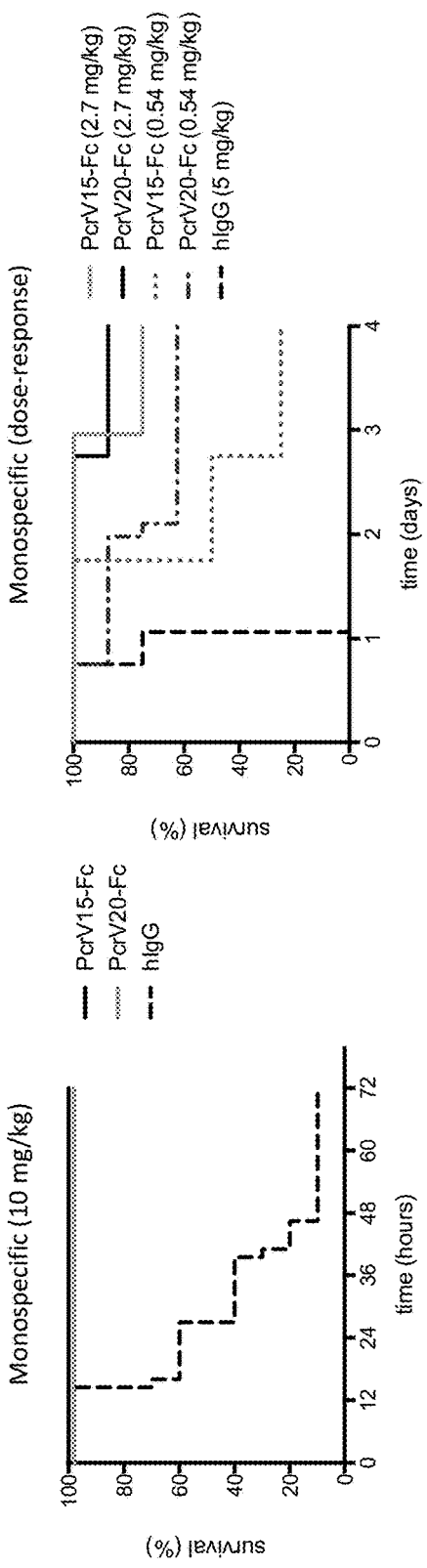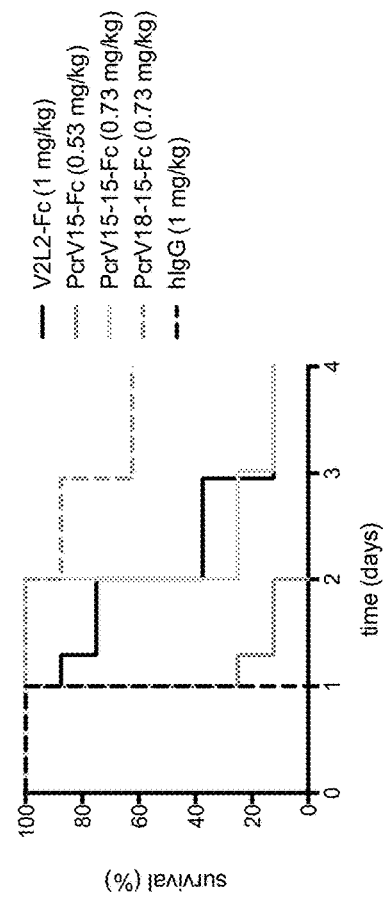

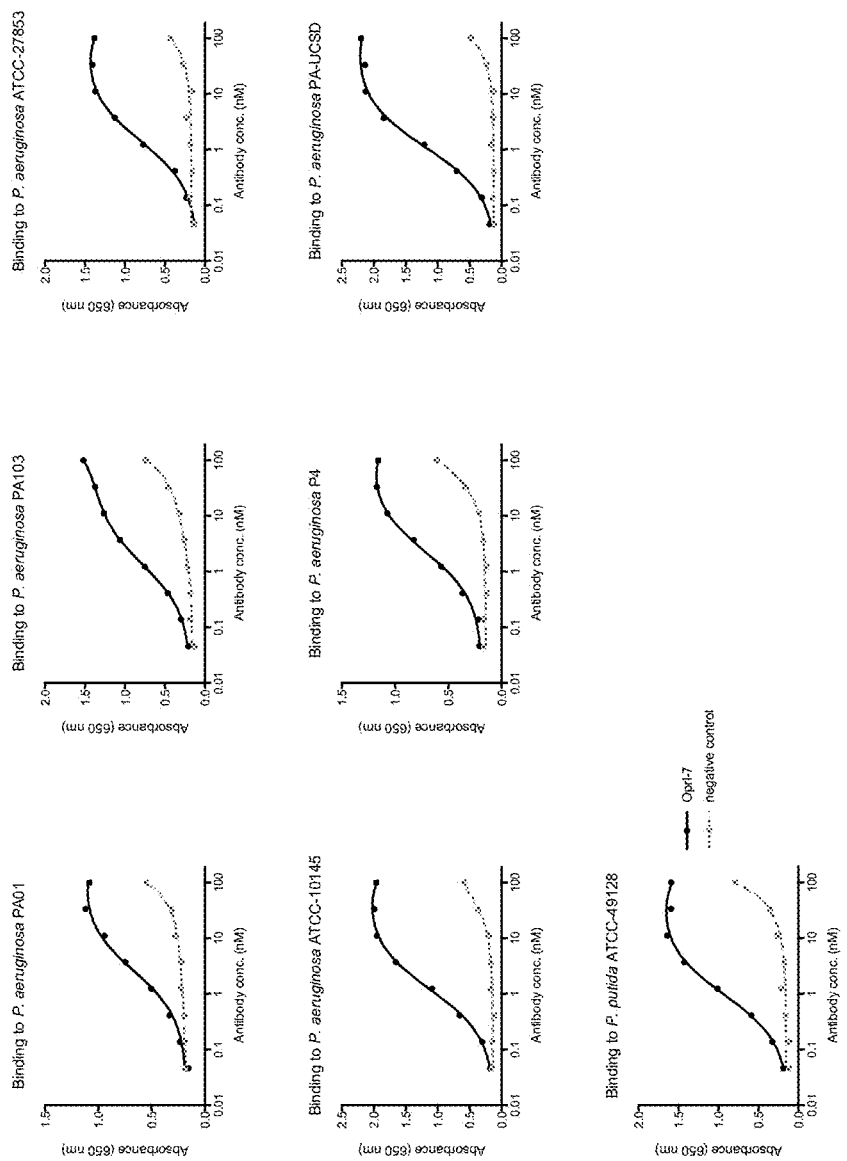

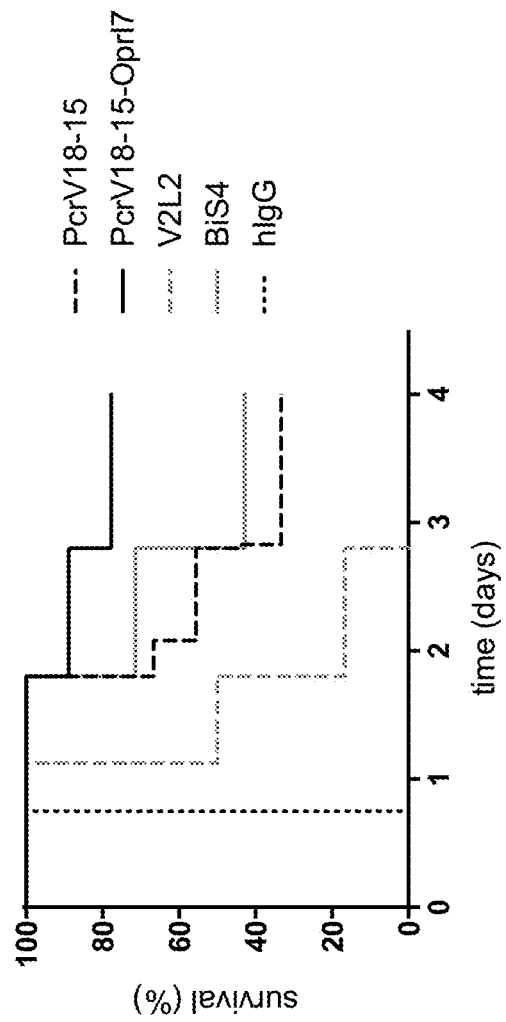

SEQUENCE LISTING

<160> NUMBER OF SEQ ID NOS: 88

<210> SEQ ID NO 1
<211> LENGTH: 218
<212> TYPE: PRT
<213> ORGANISM: Artificial Sequence
<220> FEATURE:
<223> OTHER INFORMATION: chemically synthesized

<400> SEQUENCE: 1

```
Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215
```

<210> SEQ ID NO 2

<211> LENGTH: 217
<212> TYPE: PRT
<213> ORGANISM: Artificial Sequence
<220> FEATURE:
<223> OTHER INFORMATION: chemically synthesized

<400> SEQUENCE: 2

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Lys Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 3
<211> LENGTH: 218
<212> TYPE: PRT
<213> ORGANISM: Artificial Sequence
<220> FEATURE:
<223> OTHER INFORMATION: chemically synthesized

<400> SEQUENCE: 3

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Thr Lys Gly

```
                    100                 105                 110
Gln Pro Arg Glu Pro Gln Val Tyr Thr Leu Pro Ser Arg Glu Glu
            115                 120                 125
Met Thr Lys Asn Gln Val Ser Leu Thr Cys Leu Val Lys Gly Phe Tyr
    130                 135                 140
Pro Ser Asp Ile Ala Val Glu Trp Glu Ser Gly Gln Pro Glu Asn
145                 150                 155                 160
Asn Tyr Asn Thr Thr Pro Pro Met Leu Asp Ser Asp Gly Ser Phe Phe
                165                 170                 175
Leu Tyr Ser Lys Leu Thr Val Asp Lys Ser Arg Trp Gln Gln Gly Asn
            180                 185                 190
Ile Phe Ser Cys Ser Val Met His Glu Ala Leu His Asn Arg Phe Thr
        195                 200                 205
Gln Lys Ser Leu Ser Leu Ser Pro Gly Lys
    210                 215

<210> SEQ ID NO 4
<211> LENGTH: 218
<212> TYPE: PRT
<213> ORGANISM: Artificial Sequence
<220> FEATURE:
<223> OTHER INFORMATION: chemically synthesized

<400> SEQUENCE: 4

Pro Ala Pro Glu Phe Leu Gly Gly Pro Ser Val Phe Leu Phe Pro Pro
1               5                   10                  15
Lys Pro Lys Asp Thr Leu Met Ile Ser Arg Thr Pro Glu Val Thr Cys
            20                  25                  30
Val Val Val Asp Val Ser Gln Glu Asp Pro Glu Val Gln Phe Asn Trp
        35                  40                  45
Tyr Val Asp Gly Val Glu Val His Asn Ala Lys Thr Lys Pro Arg Glu
    50                  55                  60
Glu Gln Phe Asn Ser Thr Tyr Arg Val Val Ser Val Leu Thr Val Leu
65                  70                  75                  80
His Gln Asp Trp Leu Asn Gly Lys Glu Tyr Lys Cys Lys Val Ser Asn
                85                  90                  95
Lys Gly Leu Pro Ser Ser Ile Glu Lys Thr Ile Ser Lys Ala Lys Gly
            100                 105                 110
Gln Pro Arg Glu Pro Gln Val Tyr Thr Leu Pro Pro Ser Gln Glu Glu
        115                 120                 125
Met Thr Lys Asn Gln Val Ser Leu Thr Cys Leu Val Lys Gly Phe Tyr
    130                 135                 140
Pro Ser Asp Ile Ala Val Glu Trp Glu Ser Asn Gly Gln Pro Glu Asn
145                 150                 155                 160
Asn Tyr Lys Thr Thr Pro Pro Val Leu Asp Ser Asp Gly Ser Phe Phe
                165                 170                 175
Leu Tyr Ser Arg Leu Thr Val Asp Lys Ser Arg Trp Gln Glu Gly Asn
            180                 185                 190
Val Phe Ser Cys Ser Val Met His Glu Ala Leu His Asn His Tyr Thr
        195                 200                 205
Gln Lys Ser Leu Ser Leu Ser Leu Gly Lys
    210                 215

<210> SEQ ID NO 5
<211> LENGTH: 14
<212> TYPE: PRT
```

```
<213> ORGANISM: Artificial Sequence
<220> FEATURE:
<223> OTHER INFORMATION: chemically synthesized

<400> SEQUENCE: 5

Glu Pro Lys Ser Ser Asp Lys Thr His Thr Cys Pro Pro Cys
1               5                   10

<210> SEQ ID NO 6
<211> LENGTH: 9
<212> TYPE: PRT
<213> ORGANISM: Artificial Sequence
<220> FEATURE:
<223> OTHER INFORMATION: chemically synthesized

<400> SEQUENCE: 6

Asp Lys Thr His Thr Cys Pro Pro Cys
1               5

<210> SEQ ID NO 7
<211> LENGTH: 11
<212> TYPE: PRT
<213> ORGANISM: Artificial Sequence
<220> FEATURE:
<223> OTHER INFORMATION: chemically synthesized

<400> SEQUENCE: 7

Glu Ser Lys Tyr Gly Pro Pro Cys Pro Pro Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: chemically synthesized

<400> SEQUENCE: 8

Gly Gln Gly Thr Leu Val Thr Val Lys Pro Gly Gly
1               5                   10

<210> SEQ ID NO 9
<211> LENGTH: 12
<212> TYPE: PRT
<213> ORGANISM: Artificial Sequence
<220> FEATURE:
<223> OTHER INFORMATION: chemically synthesized

<400> SEQUENCE: 9

Gly Gln Gly Thr Leu Val Thr Val Glu Pro Gly Gly
1               5                   10

<210> SEQ ID NO 10
<211> LENGTH: 124
<212> TYPE: PRT
<213> ORGANISM: Artificial Sequence
<220> FEATURE:
<223> OTHER INFORMATION: chemically synthesized

<400> SEQUENCE: 10

Glu Val Gln Leu Val Gln Ser Gly Gly Gly Leu Val Gln Ala Gly Gly
1               5                   10                  15

Ser Leu Arg Leu Ser Cys Ala Ala Ser Gly Arg Ile Phe Gly Thr Tyr
            20                  25                  30

Gly Met Gly Trp Phe Arg Gln Ala Pro Gly Lys Glu Arg Val Phe Val
        35                  40                  45
```

```
Ala Ala Ile Ser Lys Ser Gly Pro Thr Thr Tyr Tyr Ala Asp Ser Val
        50                  55                  60

Lys Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Ala Val Tyr Tyr Cys
                85                  90                  95

Gly Ala Ser Ser His Ser Met Leu Val Val Thr Thr Ser Gln Val Asp
                100                 105                 110

Tyr Trp Gly Arg Gly Thr Gln Val Thr Val Ser Ser
                115                 120
```

<210> SEQ ID NO 11
<211> LENGTH: 124
<212> TYPE: PRT
<213> ORGANISM: Artificial Sequence
<220> FEATURE:
<223> OTHER INFORMATION: chemically synthesized

<400> SEQUENCE: 11

```
Glu Val Gln Leu Val Gln Ser Gly Gly Gly Leu Val Gln Pro Gly Gly
1               5                   10                  15

Ser Leu Arg Leu Ser Cys Ala Val Ser Gly Leu Ile Phe Asp Asn Tyr
                20                  25                  30

Gly Ile Gly Trp Phe Arg Gln Ala Pro Glu Lys Glu Arg Glu Gly Val
                35                  40                  45

Ser Cys Ile His Glu Ser Asp Gly Ser Thr Tyr Tyr Thr Asp Ser Val
        50                  55                  60

Lys Gly Arg Phe Ala Ile Ser Arg Asp Asn Ala Lys Asn Thr Gly Tyr
65                  70                  75                  80

Leu Glu Met Asn Asn Leu Lys Pro Glu Asp Thr Ala Val Tyr Tyr Cys
                85                  90                  95

Val Val Leu Ser Tyr Val Ser Arg Cys Pro Glu Gly Ser Lys Tyr Asp
                100                 105                 110

Tyr Trp Gly Gln Gly Thr Gln Val Thr Val Ser Ser
                115                 120
```

<210> SEQ ID NO 12
<211> LENGTH: 125
<212> TYPE: PRT
<213> ORGANISM: Artificial Sequence
<220> FEATURE:
<223> OTHER INFORMATION: chemically synthesized

<400> SEQUENCE: 12

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
                20                  25                  30

Pro Ile Gly Trp Phe Arg Gln Ala Pro Gly Lys Glu Arg Glu Gly Val
                35                  40                  45

Ser Cys Ile Ser Ser Ser Glu Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Asn Met Lys Pro Glu Asp Thr Ala Val Tyr Tyr Cys
                85                  90                  95

Ala Thr Asp Phe Phe Thr Thr Gly Cys Pro Ser Gly Gly Gly Lys Tyr
```

```
                100             105             110
Asp Tyr Trp Gly Gln Gly Thr Gln Val Thr Val Ser Ser
        115             120             125

<210> SEQ ID NO 13
<211> LENGTH: 121
<212> TYPE: PRT
<213> ORGANISM: Artificial Sequence
<220> FEATURE:
<223> OTHER INFORMATION: chemically synthesized

<400> SEQUENCE: 13

Glu Val Gln Leu Val Gln Ser Gly Gly Gly Leu Val Arg Ala Gly Gly
1               5                   10                  15

Ser Leu Arg Leu Ser Cys Ala Pro Ser Glu Arg Thr Phe Gly Ser Phe
            20                  25                  30

Gly Met Gly Trp Phe Arg Gln Ala Pro Gly Lys Glu Arg Glu Phe Val
        35                  40                  45

Ala Ala Leu Met Trp Gly Thr Ser Tyr Thr Ser Tyr Ala Asp Ser Val
    50                  55                  60

Lys Gly Arg Phe Thr Val Ser Lys Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Gly Ala Val Gly Ala Asp Pro Arg Arg Tyr Asp Tyr Trp Gly
            100                 105                 110

Gln Gly Thr Gln Val Thr Val Ser Ser
        115                 120

<210> SEQ ID NO 14
<211> LENGTH: 126
<212> TYPE: PRT
<213> ORGANISM: Artificial Sequence
<220> FEATURE:
<223> OTHER INFORMATION: chemically synthesized

<400> SEQUENCE: 14

Glu Val Gln Leu Val Gln Ser Gly Gly Gly Leu Val Gln Ala Gly Gly
1               5                   10                  15

Ser Leu Arg Leu Ser Cys Ala Ala Ser Gly Leu Ala Phe Arg Asn Tyr
            20                  25                  30

Arg Met Gly Trp Phe Arg Gln Ala Pro Gly Lys Glu Arg Glu Phe Val
        35                  40                  45

Ala Ala Ile Ser Gly Asn Ile Gly Gly Ser Gly Val Gly Thr Asp Tyr
    50                  55                  60

Ala Asp Ser Val Lys Gly Arg Phe Thr Ile Ser Arg Asp Asn Asp Lys
65                  70                  75                  80

Asp Thr Ala Tyr Leu Gln Met Asn Ser Leu Lys Pro Glu Asp Thr Ala
                85                  90                  95

Val Tyr Tyr Cys Ala Ala Asp His His Leu Thr Met Leu Pro Gly Glu
            100                 105                 110

Tyr Asp Phe Trp Gly Glu Gly Thr Gln Val Thr Val Ser Ser
        115                 120                 125

<210> SEQ ID NO 15
<211> LENGTH: 126
<212> TYPE: PRT
<213> ORGANISM: Artificial Sequence
<220> FEATURE:
```

<223> OTHER INFORMATION: chemically synthesized

<400> SEQUENCE: 15

```
Glu Val Gln Leu Val Gln Ser Gly Gly Gly Leu Val Gln Pro Gly Gly
1               5                   10                  15
Ser Leu Arg Leu Ser Cys Ala Ala Ser Gly Ser Thr Leu Asp Tyr Tyr
            20                  25                  30
Ala Ile Gly Trp Phe Arg Gln Ala Pro Gly Lys Glu Arg Glu Gly Val
        35                  40                  45
Ala Cys Ile Ser Ser Ser Asp Gly Ser Thr Asp Tyr Ala Asp Ser Met
    50                  55                  60
Lys Gly Arg Phe Thr Ile Ser Arg Asp Asn Ala Gln Lys Thr Val Tyr
65                  70                  75                  80
Leu Gln Met Asn Ser Leu Lys Pro Glu Asp Thr Ala Val Tyr Ser Cys
                85                  90                  95
Ala Ala Val Ala Phe Phe Cys Gly Ser Ser Trp Tyr Leu Ser Ser Gly
            100                 105                 110
Met Asp Tyr Trp Gly Lys Gly Thr Gln Val Thr Val Ser Ser
        115                 120                 125
```

<210> SEQ ID NO 16
<211> LENGTH: 120
<212> TYPE: PRT
<213> ORGANISM: Artificial Sequence
<220> FEATURE:
<223> OTHER INFORMATION: chemically synthesized

<400> SEQUENCE: 16

```
Glu Val Gln Leu Val Gln Ser Gly Gly Gly Leu Val Gln Ala Gly Gly
1               5                   10                  15
Ser Leu Arg Leu Ser Cys Ala Ala Ser Gly Gly Thr Phe Ser Ser Asn
            20                  25                  30
Ala Met Tyr Trp Tyr Arg Gln Ala Pro Gly Lys Gln Arg Glu Leu Val
        35                  40                  45
Ala Ser Ile Ser Gly Thr Ser Asn Ala Asn Tyr Pro Asp Ser Val Lys
    50                  55                  60
Gly Arg Phe Thr Ile Ser Arg Asp Asn Ala Lys Asn Thr Val Thr Leu
65                  70                  75                  80
Gln Met Asn Ser Leu Lys Pro Glu Asp Thr Ala Val Tyr Tyr Cys Arg
                85                  90                  95
Ala Ala Pro Val Ser Gly Pro Leu Ile Gly Arg Ile Phe Trp Gly Gln
            100                 105                 110
Gly Thr Gln Val Thr Val Ser Ser
        115                 120
```

<210> SEQ ID NO 17
<211> LENGTH: 126
<212> TYPE: PRT
<213> ORGANISM: Artificial Sequence
<220> FEATURE:
<223> OTHER INFORMATION: chemically synthesized

<400> SEQUENCE: 17

```
Glu Val Gln Leu Val Gln Ser Gly Gly Gly Leu Val Gln Ala Gly Gly
1               5                   10                  15
Ser Leu Arg Leu Ser Cys Ala Thr Ser Gly Leu Thr Phe Ser Val Tyr
            20                  25                  30
Ala Met Gly Trp Phe Arg Gln Ala Pro Gly Lys Gln Arg Glu Phe Val
```

```
            35                  40                  45

Ala Arg Ile Thr Ala Gly Gly Ser Gly Thr Tyr Tyr Ala Asp Ser Met
    50                  55                  60

Glu Gly Arg Phe Thr Ile Ser Arg Asp Asn Ala Arg Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Arg His Trp Thr Arg Gly Thr Glu His Leu Pro Thr Ala
            100                 105                 110

Tyr Asp Tyr Trp Gly Gln Gly Thr Gln Val Thr Val Ser Ser
        115                 120                 125

<210> SEQ ID NO 18
<211> LENGTH: 111
<212> TYPE: PRT
<213> ORGANISM: Artificial Sequence
<220> FEATURE:
<223> OTHER INFORMATION: chemically synthesized

<400> SEQUENCE: 18

Glu Val Gln Leu Val Gln Ser Gly Gly Gly Leu Val Gln Ala Gly Gly
1               5                   10                  15

Ser Leu Arg Leu Ser Cys Ala Ser Ser Gly Ser Thr Phe Arg Thr Tyr
            20                  25                  30

Gly Met Gly Trp Phe Arg Gln Pro Pro Gly Lys Gln Arg Glu Trp Val
        35                  40                  45

Ala Gly Met Ala Ile Asp Gly Leu Thr Thr Tyr Ala Asp Ser Ala Lys
    50                  55                  60

Gly Arg Phe Thr Ala Ser Arg Asp Asn Ala Arg Asn Ile Val Tyr Leu
65                  70                  75                  80

Gln Met Asn Glu Leu Lys Pro Glu Asp Thr Ala Val Tyr Tyr Cys Tyr
                85                  90                  95

Ala Ala Gly Tyr Trp Gly Gln Gly Thr Gln Val Thr Val Ser Ser
            100                 105                 110

<210> SEQ ID NO 19
<211> LENGTH: 120
<212> TYPE: PRT
<213> ORGANISM: Artificial Sequence
<220> FEATURE:
<223> OTHER INFORMATION: chemically synthesized

<400> SEQUENCE: 19

Glu Val Gln Leu Val Gln Ser Gly Gly Gly Leu Val Gln Ala Gly Gly
1               5                   10                  15

Ser Leu Arg Leu Ser Cys Thr Thr Ser Gly Ile Thr Phe Ser Asp Asn
            20                  25                  30

Ala Met Tyr Trp Tyr Arg Gln Ala Pro Gly Lys Gln Arg Glu Leu Val
        35                  40                  45

Ala Ser Ile Ser Ser Gly Gly Trp Thr Asn Tyr Ala Asp Ser Val Lys
    50                  55                  60

Gly Arg Phe Thr Ile Ser Arg Asp Asn Val Lys Asn Thr Val Thr Leu
65                  70                  75                  80

Gln Met Asn Ser Leu Glu Pro Glu Asp Thr Ala Leu Tyr Tyr Cys Arg
                85                  90                  95

Ala Ala Pro Val Arg Gly Asn Phe Ile Gly Arg Val Phe Trp Gly Gln
            100                 105                 110
```

```
Gly Thr Gln Val Thr Val Ser Ser
        115                 120
```

<210> SEQ ID NO 20
<211> LENGTH: 123
<212> TYPE: PRT
<213> ORGANISM: Artificial Sequence
<220> FEATURE:
<223> OTHER INFORMATION: chemically synthesized

<400> SEQUENCE: 20

```
Glu Val Gln Leu Val Gln Ser Gly Gly Gly Leu Val Gln Pro Gly Gly
1               5                   10                  15

Ser Leu Arg Leu Ser Cys Ala Ala Phe Gly Ser Ile Phe Thr Ile Gly
            20                  25                  30

Thr Met Gly Trp Tyr Arg Gln Ala Pro Gly Lys Gln Arg Glu Leu Val
        35                  40                  45

Ala Thr Ile Thr Arg Gly Ser Ser Thr Asn Tyr Ala Asp Ser Val Lys
    50                  55                  60

Gly Arg Phe Thr Ile Ser Ile Asp Ser Ala Lys Asn Thr Val Tyr Leu
65                  70                  75                  80

Gln Met Asn Ser Leu Lys Ser Glu Asp Thr Ala Val Tyr Tyr Cys Ala
                85                  90                  95

Ala Asp Arg Gly Ala Val Gly Pro Ala Met Arg Val Val Ala Asp Tyr
            100                 105                 110

Trp Gly Gln Gly Thr Gln Val Thr Val Ser Ser
        115                 120
```

<210> SEQ ID NO 21
<211> LENGTH: 124
<212> TYPE: PRT
<213> ORGANISM: Artificial Sequence
<220> FEATURE:
<223> OTHER INFORMATION: chemically synthesized

<400> SEQUENCE: 21

```
Glu Val Gln Leu Val Gln Ser Gly Gly Gly Leu Val Gln Ala Gly Gly
1               5                   10                  15

Ser Leu Arg Leu Ser Cys Ala Ala Ser Gly Ser Thr Phe Ser Ser Asn
            20                  25                  30

Ala Met Tyr Trp Tyr Arg Gln Ala Pro Gly Lys Gln Arg Glu Leu Val
        35                  40                  45

Ala Ser Ile Ser Asp Gly Gly Phe Thr Thr Tyr Ala Asp Ser Val
    50                  55                  60

Lys Gly Arg Phe Thr Ile Ser Lys Asp Asn Ala Glu Asn Thr Val Tyr
65                  70                  75                  80

Leu Gln Met Asn Ile Met Lys Pro Glu Asp Thr Ala Val Tyr Tyr Cys
                85                  90                  95

Ala Ala Ser Ile Ser Ser Arg Val Val Val His Thr Ala Gln Ala Asp
            100                 105                 110

Tyr Trp Gly Gln Gly Thr Gln Val Thr Val Ser Ser
        115                 120
```

<210> SEQ ID NO 22
<211> LENGTH: 121
<212> TYPE: PRT
<213> ORGANISM: Artificial Sequence
<220> FEATURE:
<223> OTHER INFORMATION: chemically synthesized

<400> SEQUENCE: 22

Glu Val Gln Leu Val Gln Ser Gly Gly Gly Leu Val Gln Pro Gly Gly
1               5                   10                  15

Ser Leu Arg Leu Pro Cys Ala Ala Ser Gly Ser Ile Phe Thr Ile Gly
            20                  25                  30

Thr Met Gly Trp Tyr Arg Gln Ala Pro Gly Lys Gln Arg Glu Leu Val
        35                  40                  45

Ala Thr Ile Thr Arg Gly Ser Ser Thr Asn Tyr Ala Asp Ser Val Lys
    50                  55                  60

Asp Arg Phe Thr Ile Ser Arg Asp Asn Ala Lys Arg Thr Leu His Leu
65                  70                  75                  80

Gln Met Asn Gly Leu Lys Ala Glu Asp Thr Ala Val Tyr Tyr Cys Ala
                85                  90                  95

Thr Asp Leu Phe Glu Asn Ser Cys Pro Leu Lys His Asp Phe Trp Gly
            100                 105                 110

Gln Gly Thr Gln Val Thr Val Ser Ser
        115                 120

<210> SEQ ID NO 23
<211> LENGTH: 119
<212> TYPE: PRT
<213> ORGANISM: Artificial Sequence
<220> FEATURE:
<223> OTHER INFORMATION: chemically synthesized

<400> SEQUENCE: 23

Glu Val Gln Leu Val Gln Ser Gly Gly Gly Leu Val Gln Ala Gly Gly
1               5                   10                  15

Ser Leu Arg Leu Ser Cys Ala Ala Ser Arg Ile Thr Phe Ala Leu Tyr
            20                  25                  30

Val Ile Asp Trp Tyr Arg Gln Thr Pro Glu Ser Gln Arg Glu Leu Val
        35                  40                  45

Ala Arg Ile Arg Pro Glu Gly Leu Ala Val Tyr Ala Asp Ser Val Lys
    50                  55                  60

Gly Arg Phe Thr Ile Ser Arg Asp Asn Gly Arg Asn Thr Ala Tyr Leu
65                  70                  75                  80

Gln Met Asn Ser Leu Gln Glu Glu Asp Thr Ala Val Tyr Tyr Cys His
                85                  90                  95

Ala Asp Pro Val Phe Thr Pro Gly Arg Asn Asp Tyr Trp Gly Gln Gly
            100                 105                 110

Thr Gln Val Thr Val Ser Ser
        115

<210> SEQ ID NO 24
<211> LENGTH: 121
<212> TYPE: PRT
<213> ORGANISM: Artificial Sequence
<220> FEATURE:
<223> OTHER INFORMATION: chemically synthesized

<400> SEQUENCE: 24

Glu Val Gln Leu Val Gln Ser Gly Gly Gly Leu Val Gln Pro Gly Glu
1               5                   10                  15

Ser Leu Arg Leu Ser Cys Ala Ala Ser Gly Ser Ile Phe Ser Ile Asn
            20                  25                  30

Thr Met Val Trp Tyr Arg Gln Val Pro Gly Lys Gln Arg Glu Leu Val
        35                  40                  45

Ala Ser Ile Thr Asn Gln Gly Ile Pro His Tyr Ala Asp Ser Val Lys
         50                  55                  60

Gly Arg Phe Thr Ile Ser Arg Glu Asn Ala Lys Asn Thr Val Asn Leu
 65                  70                  75                  80

Gln Met Asn Ser Leu Lys Pro Glu Asp Thr Ala Val Tyr Val Cys Asn
                 85                  90                  95

Ala Trp Ile Arg Ser Asp Gly Val Ser Pro Tyr Leu Asn Tyr Trp Gly
                100                 105                 110

Gln Gly Thr Gln Val Thr Val Ser Ser
        115                 120

<210> SEQ ID NO 25
<211> LENGTH: 114
<212> TYPE: PRT
<213> ORGANISM: Artificial Sequence
<220> FEATURE:
<223> OTHER INFORMATION: chemically synthesized

<400> SEQUENCE: 25

Glu Val Gln Leu Val Gln Ser Gly Gly Gly Leu Val Gln Pro Gly Gly
 1               5                  10                  15

Ser Leu Gly Leu Ser Cys Val Ser Gly Ser Ile Ser Gly Ile His
                 20                  25                  30

Thr Met Gly Trp Tyr Arg Arg Ala Pro Gly Asn Gln Arg Glu Leu Ile
             35                  40                  45

Ala Thr Ala Thr Ser Ala Gly Ile Thr Asn Tyr Ser Glu Ser Val Lys
         50                  55                  60

Gly Arg Phe Thr Ile Ser Arg Asp Asn Ala Lys Ser Thr Val Tyr Leu
 65                  70                  75                  80

Gln Met Ser Ser Leu Lys Pro Glu Asp Thr Gly Val Tyr Tyr Cys Asn
                 85                  90                  95

Asp Val Phe Gly Arg Thr Ser Trp Gly Gln Gly Thr Gln Val Thr Val
                100                 105                 110

Ser Ser

<210> SEQ ID NO 26
<211> LENGTH: 116
<212> TYPE: PRT
<213> ORGANISM: Artificial Sequence
<220> FEATURE:
<223> OTHER INFORMATION: chemically synthesized

<400> SEQUENCE: 26

Glu Val Gln Leu Val Gln Ser Gly Gly Gly Leu Val Gln Pro Gly Gly
 1               5                  10                  15

Ser Leu Arg Leu Ser Cys Ala Ala Ser Gly Asn Ile Phe Gly Gly Asn
                 20                  25                  30

Val Met Gly Trp Tyr Arg Gln Ala Pro Gly Lys Gln Arg Glu Leu Val
             35                  40                  45

Ala Gly Ile Gly Ser Leu Gly Arg Thr Thr Tyr Ala Asp Ser Val Lys
         50                  55                  60

Gly Arg Phe Ser Ile Ser Arg Asp Asn Ala Lys Asn Thr Val Tyr Leu
 65                  70                  75                  80

Gln Met Asp Ser Leu Lys Pro Glu Asp Thr Ala Val Tyr Tyr Cys Asn
                 85                  90                  95

Val Val Arg Leu Gly Gly Pro Tyr Trp Gly Gln Gly Thr Gln Val
                100                 105                 110

Thr Val Ser Ser
        115

<210> SEQ ID NO 27
<211> LENGTH: 120
<212> TYPE: PRT
<213> ORGANISM: Artificial Sequence
<220> FEATURE:
<223> OTHER INFORMATION: chemically synthesized

<400> SEQUENCE: 27

Glu Val Gln Leu Val Gln Ser Gly Gly Gly Leu Val Gln Ala Gly Gly
1               5                   10                  15

Ser Leu Arg Leu Ser Cys Thr Thr Ser Gly Asn Thr Phe Ser Asp Asn
            20                  25                  30

Ala Met Tyr Trp Tyr Arg Gln Ala Pro Gly Lys Gln Arg Glu Gln Val
        35                  40                  45

Ala Ser Ile Ser Ser Gly Gly Trp Thr Asn Tyr Ala Asp Ser Val Lys
    50                  55                  60

Gly Arg Phe Thr Ile Ser Arg Asp Asn Val Lys Asn Thr Val Thr Leu
65                  70                  75                  80

Gln Met Asp Arg Leu Glu Pro Glu Asp Thr Ala Leu Tyr Tyr Cys Arg
                85                  90                  95

Ala Ala Pro Val Arg Gly Tyr Leu Ile Gly Arg Val Phe Trp Gly Gln
            100                 105                 110

Gly Thr Gln Val Thr Val Ser Ser
        115                 120

<210> SEQ ID NO 28
<211> LENGTH: 117
<212> TYPE: PRT
<213> ORGANISM: Artificial Sequence
<220> FEATURE:
<223> OTHER INFORMATION: chemically synthesized

<400> SEQUENCE: 28

Glu Val Gln Leu Val Gln Ser Gly Gly Gly Leu Val Gln Ala Gly Gly
1               5                   10                  15

Ser Leu Arg Leu Ser Cys Ser Ala Ser Gly Ser Asn Ser Ile Phe Asn
            20                  25                  30

Met Gly Trp Tyr Arg Gln Arg Pro Gly Arg Gln Arg Glu Leu Val Ala
        35                  40                  45

Leu Ile Ser Ser Gly Thr Gly Ser Thr Ser Tyr Ala Gly Ser Val Lys
    50                  55                  60

Gly Arg Phe Ala Ile Ser Arg Asp Asn Ala Lys Ala Thr Val Tyr Leu
65                  70                  75                  80

Gln Met Asn Ser Leu Lys Leu Glu Asp Thr Ala Val Tyr Tyr Cys Arg
                85                  90                  95

Ile Thr Thr Asp Asn Ala Arg Leu Val Tyr Trp Gly Gln Gly Thr Gln
            100                 105                 110

Val Thr Val Ser Ser
        115

<210> SEQ ID NO 29
<211> LENGTH: 121
<212> TYPE: PRT
<213> ORGANISM: Artificial Sequence
<220> FEATURE:
<223> OTHER INFORMATION: chemically synthesized

<400> SEQUENCE: 29

Glu Val Gln Leu Val Gln Ser Gly Gly Gly Leu Val Gln Pro Gly Gly
1               5                   10                  15

Ser Leu Arg Leu Ser Cys Ala Ala Ser Gly Arg Ile Phe Ser Val Asn
            20                  25                  30

Asn Met Gly Trp Tyr Arg Gln Thr Pro Gly Lys Gln Arg Glu Leu Val
        35                  40                  45

Ala Val Ile Thr Val Asn Gly Ile Thr Thr Tyr Ser Asp Ser Val Lys
    50                  55                  60

Gly Arg Phe Thr Leu Ser Arg Asp Asn Ala Lys Asn Thr Ile Tyr Leu
65                  70                  75                  80

Gln Met Asn Ser Leu Lys Pro Glu Asp Thr Ala Val Tyr Ser Cys Tyr
                85                  90                  95

Gly Tyr Ile Arg Leu Ala Ala Thr Asn Pro Tyr Val Gln Tyr Trp Gly
            100                 105                 110

Gln Gly Thr Gln Val Thr Val Ser Ser
        115                 120

<210> SEQ ID NO 30
<211> LENGTH: 121
<212> TYPE: PRT
<213> ORGANISM: Artificial Sequence
<220> FEATURE:
<223> OTHER INFORMATION: chemically synthesized

<400> SEQUENCE: 30

Glu Val Gln Leu Val Gln Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Asn Gln Arg Asp Ile Val
        35                  40                  45

Ala Thr Ile Thr Met Asn Gly Val Pro His Tyr Ala Asp Ala Val Lys
    50                  55                  60

Gly Arg Phe Thr Ile Ser Arg Asp Asn Ala Lys Asn Thr Val Tyr Leu
65                  70                  75                  80

Gln Met Asn Gly Leu Lys Pro Glu Asp Thr Ala Val Tyr Tyr Cys Asn
                85                  90                  95

Ala Trp Ile Asn Leu Tyr Gly Ser Pro Pro Leu Gln Asn Tyr Trp Gly
            100                 105                 110

Gln Gly Thr Gln Val Thr Val Ser Ser
        115                 120

<210> SEQ ID NO 31
<211> LENGTH: 121
<212> TYPE: PRT
<213> ORGANISM: Artificial Sequence
<220> FEATURE:
<223> OTHER INFORMATION: chemically synthesized

<400> SEQUENCE: 31

Glu Val Gln Leu Val Gln Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Thr Ser Ile Thr Asn Gln Gly Ile Pro His Tyr Ala Asp Ser Val Lys
        50                  55                  60

Gly Arg Phe Thr Ile Ser Arg Glu Asn Ala Lys Asn Thr Val Asn Leu
65                  70                  75                  80

Gln Met Asn Ser Leu Lys Pro Glu Asp Thr Ala Val Tyr Val Cys Asn
                85                  90                  95

Ala Trp Ile Arg Gly Asp Gly Ser Pro Tyr Leu Asn Tyr Trp Gly
            100                 105                 110

Gln Gly Thr Gln Val Thr Val Ser Ser
        115                 120

<210> SEQ ID NO 32
<211> LENGTH: 121
<212> TYPE: PRT
<213> ORGANISM: Artificial Sequence
<220> FEATURE:
<223> OTHER INFORMATION: chemically synthesized

<400> SEQUENCE: 32

Glu Val Gln Leu Val Gln Ser Gly Gly Gly Leu Val Gln Pro Gly Glu
1               5                   10                  15

Ser Leu Arg Leu Ser Cys Ala Ala Ser Gly Ser Ile Phe Ser Ile Asn
            20                  25                  30

Thr Met Val Trp Tyr Arg Gln Val Pro Gly Lys Gln Arg Glu Leu Val
        35                  40                  45

Ala Ser Ile Thr Asn Gln Gly Ile Pro His Tyr Ala Asp Ser Val Lys
    50                  55                  60

Gly Arg Phe Thr Ile Ser Arg Glu Asn Ala Lys Asn Thr Val Asn Leu
65                  70                  75                  80

Gln Met Asn Ser Leu Lys Pro Glu Asp Thr Ala Val Tyr Val Cys Asn
                85                  90                  95

Ala Trp Ile Arg Ser Asp Gly Val Pro Pro Tyr Leu Asn Tyr Trp Gly
            100                 105                 110

Gln Gly Thr Gln Val Thr Val Ser Ser
        115                 120

<210> SEQ ID NO 33
<211> LENGTH: 122
<212> TYPE: PRT
<213> ORGANISM: Artificial Sequence
<220> FEATURE:
<223> OTHER INFORMATION: chemically synthesized

<400> SEQUENCE: 33

Glu Val Gln Leu Val Gln Ser Gly Gly Gly Leu Val Gln Pro Gly Gly
1               5                   10                  15

Ser Leu Arg Leu Ser Cys Ala Ala Ser Gly Ser Ile Phe Asn Ile Asn
            20                  25                  30

Ser Met His Trp Tyr Arg Gln Ala Pro Gly Asn Gln Arg Glu Leu Val
        35                  40                  45

Ala Ser Ile Ser Lys Gly Gly Ile Thr Asn Tyr Ala Asp Ser Val Lys
    50                  55                  60

Gly Arg Phe Ala Ile Ser Arg Asp Asp Ala Gln Asn Thr Leu Tyr Leu
65                  70                  75                  80

Gln Met Asn Ser Leu Lys Pro Glu Asp Thr Ala Val Tyr Tyr Cys Asn
                85                  90                  95

Ala Trp Ile Ser Glu Ile Ala Thr Gly Pro Ile Leu Tyr Asn Tyr Trp
            100                 105                 110

Gly Gln Gly Thr Gln Val Thr Val Ser Ser
            115                 120

<210> SEQ ID NO 34
<211> LENGTH: 121
<212> TYPE: PRT
<213> ORGANISM: Artificial Sequence
<220> FEATURE:
<223> OTHER INFORMATION: chemically synthesized

<400> SEQUENCE: 34

Glu Val Gln Leu Val Gln Ser Gly Gly Leu Val Gln Pro Gly Gly
1               5                   10                  15

Ser Leu Ser Leu Ser Cys Ala Ala Ser Gly Ser Val Phe Ser Ile Asn
            20                  25                  30

Arg Met Ala Trp Tyr Arg Gln Ala Pro Gly Lys Gln Arg Glu Leu Val
            35                  40                  45

Ala Asp Ile Gly Thr Met Gly Ala Ser Asp Tyr Ala Asp Ser Val Lys
        50                  55                  60

Gly Arg Phe Thr Ile Ser Arg Asp Asn Ala Lys Lys Thr Val Asp Leu
65                  70                  75                  80

Gln Met Asn Ser Leu Lys Pro Glu Asp Thr Ala Val Tyr Phe Cys Asn
                85                  90                  95

Ala Trp Met Arg Gly Ala Pro Asp Val Ala Tyr Thr Asn Tyr Trp Gly
            100                 105                 110

Gln Gly Thr Gln Val Thr Val Ser Ser
            115                 120

<210> SEQ ID NO 35
<211> LENGTH: 121
<212> TYPE: PRT
<213> ORGANISM: Artificial Sequence
<220> FEATURE:
<223> OTHER INFORMATION: chemically synthesized

<400> SEQUENCE: 35

Glu Val Gln Leu Val Gln Ser Gly Gly Gly Leu Val Gln Pro Gly Gly
1               5                   10                  15

Ser Leu Arg Leu Ser Cys Ala Ala Ser Gly Arg Val Val Ser Ile Asn
            20                  25                  30

Asn Met Gly Trp Tyr Gln Gln Thr Pro Gly Asn Gln Arg Glu Leu Val
            35                  40                  45

Ala Ile Ile Thr Leu Asn Gly Val Thr Thr Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Ala Ser Leu Lys Pro Glu Asp Thr Ala Ile Tyr Tyr Cys Asn
                85                  90                  95

Ala Trp Val Arg Thr Val Pro Gly Ser Ala Tyr Ser Asn Tyr Trp Gly
            100                 105                 110

Gln Gly Thr Gln Val Thr Val Ser Ser
            115                 120

<210> SEQ ID NO 36
<211> LENGTH: 121
<212> TYPE: PRT
<213> ORGANISM: Artificial Sequence
<220> FEATURE:
<223> OTHER INFORMATION: chemically synthesized

<400> SEQUENCE: 36

Glu Val Gln Leu Val Gln Ser Gly Gly Asp Leu Val Gln Pro Gly Gly
1               5                   10                  15

Ser Leu Arg Leu Ser Cys Ala Ala Ser Gly Arg Ile Phe Ser Val Asn
            20                  25                  30

Asn Met Gly Trp Tyr Arg Gln Ala Pro Gly Lys Gln Arg Glu Leu Val
        35                  40                  45

Ala Val Ile Thr Met Asn Gly Val Thr Thr Tyr Glu Asp Ser Val Lys
    50                  55                  60

Gly Arg Phe Thr Leu Ser Arg Asp Asn Ala Lys Asn Thr Ile Tyr Leu
65                  70                  75                  80

Gln Met Asn Ser Leu Lys Pro Glu Asp Thr Ala Val Tyr Phe Cys Tyr
                85                  90                  95

Gly Tyr Ile Arg Leu Ala Ala Thr Asn Pro Tyr Val Gln Tyr Trp Gly
            100                 105                 110

Gln Gly Thr Gln Val Thr Val Ser Ser
        115                 120

<210> SEQ ID NO 37
<211> LENGTH: 121
<212> TYPE: PRT
<213> ORGANISM: Artificial Sequence
<220> FEATURE:
<223> OTHER INFORMATION: chemically synthesized

<400> SEQUENCE: 37

Glu Val Gln Leu Leu Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Thr Met Val Trp Tyr Arg Gln Ala Pro Gly Lys Gln Arg Glu Leu Val
        35                  40                  45

Ser Ser Ile Thr Asn Gln Gly Ile Pro His Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Ala Trp Ile Arg Ser Asp Gly Val Ser Pro Tyr Leu Asn Tyr Trp Gly
            100                 105                 110

Gln Gly Thr Leu Val Thr Val Lys Pro
        115                 120

<210> SEQ ID NO 38
<211> LENGTH: 121
<212> TYPE: PRT
<213> ORGANISM: Artificial Sequence
<220> FEATURE:
<223> OTHER INFORMATION: chemically synthesized

<400> SEQUENCE: 38

Glu Val Gln Leu Leu Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Thr Met Val Trp Tyr Arg Gln Ala Pro Gly Lys Gln Arg Glu Leu Val
        35                  40                  45

Ser Ser Ile Thr Asn Gln Gly Ile Pro His Tyr Ala Glu Ser Val Lys
            50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Asn
                 85                  90                  95

Ala Trp Ile Arg Ser Tyr Gly Val Ser Pro Tyr Leu Asn Tyr Trp Gly
            100                 105                 110

Gln Gly Thr Leu Val Thr Val Lys Pro
            115                 120

<210> SEQ ID NO 39
<211> LENGTH: 121
<212> TYPE: PRT
<213> ORGANISM: Artificial Sequence
<220> FEATURE:
<223> OTHER INFORMATION: chemically synthesized

<400> SEQUENCE: 39

Glu Val Gln Leu Leu Glu Ser Gly Gly Gly Val Gln Pro Gly Gly
 1               5                  10                  15

Ser Leu Arg Leu Ser Cys Ala Ala Ser Gly Ser Ile Phe Ser Ile Asn
             20                  25                  30

Thr Met Val Trp Tyr Arg Gln Ala Pro Gly Lys Gln Arg Glu Leu Val
         35                  40                  45

Ser Ser Ile Thr Asn Gln Gly Ile Pro His Tyr Ala Glu Ser Val Lys
            50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Asn
                 85                  90                  95

Ala Trp Ile Arg Ser Glu Gly Val Ser Pro Tyr Leu Asn Tyr Trp Gly
            100                 105                 110

Gln Gly Thr Leu Val Thr Val Lys Pro
            115                 120

<210> SEQ ID NO 40
<211> LENGTH: 121
<212> TYPE: PRT
<213> ORGANISM: Artificial Sequence
<220> FEATURE:
<223> OTHER INFORMATION: chemically synthesized

<400> SEQUENCE: 40

Glu Val Gln Leu Leu Glu Ser Gly Gly Gly Val Gln Pro Gly Gly
 1               5                  10                  15

Ser Leu Arg Leu Ser Cys Ala Ala Ser Gly Ser Ile Phe Ser Ile Asn
             20                  25                  30

Thr Met Val Trp Tyr Arg Gln Ala Pro Gly Lys Gln Arg Glu Leu Val
         35                  40                  45

Ser Ser Ile Thr Asn Gln Gly Ile Pro His Tyr Ala Glu Ser Val Lys
            50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Asn
                 85                  90                  95

Ala Trp Ile Arg Ser Gln Gly Val Ser Pro Tyr Leu Asn Tyr Trp Gly

```
                 100                 105                 110

Gln Gly Thr Leu Val Thr Val Lys Pro
        115                 120

<210> SEQ ID NO 41
<211> LENGTH: 121
<212> TYPE: PRT
<213> ORGANISM: Artificial Sequence
<220> FEATURE:
<223> OTHER INFORMATION: chemically synthesized

<400> SEQUENCE: 41

Glu Val Gln Leu Leu Glu Ser Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Val Trp Tyr Arg Gln Ala Pro Gly Lys Gln Arg Glu Leu Val
            35                  40                  45

Ser Ser Ile Thr Asn Gln Gly Ile Pro His Tyr Ala Glu Ser Val Lys
        50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Ala Trp Ile Arg Ser Asp Ala Val Ser Pro Tyr Leu Asn Tyr Trp Gly
            100                 105                 110

Gln Gly Thr Leu Val Thr Val Lys Pro
        115                 120

<210> SEQ ID NO 42
<211> LENGTH: 121
<212> TYPE: PRT
<213> ORGANISM: Artificial Sequence
<220> FEATURE:
<223> OTHER INFORMATION: chemically synthesized

<400> SEQUENCE: 42

Glu Val Gln Leu Leu Glu Ser Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Val Trp Tyr Arg Gln Ala Pro Gly Lys Gln Arg Glu Leu Val
            35                  40                  45

Ser Ser Ile Thr Asn Gln Gly Ile Pro His Tyr Ala Glu Ser Val Lys
        50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Ala Trp Ile Arg Ser Asp Thr Val Ser Pro Tyr Leu Asn Tyr Trp Gly
            100                 105                 110

Gln Gly Thr Leu Val Thr Val Lys Pro
        115                 120

<210> SEQ ID NO 43
<211> LENGTH: 120
<212> TYPE: PRT
<213> ORGANISM: Artificial Sequence
<220> FEATURE:
```

-continued

<223> OTHER INFORMATION: chemically synthesized

<400> SEQUENCE: 43

Glu Val Gln Leu Leu Glu Ser Gly Gly Gly Glu Val Gln Pro Gly Gly
1               5                   10                  15

Ser Leu Arg Leu Ser Cys Ala Ala Ser Gly Asn Thr Phe Ser Asp Asn
            20                  25                  30

Ala Met Tyr Trp Tyr Arg Gln Ala Pro Gly Lys Gln Arg Glu Leu Val
        35                  40                  45

Ser Ser Ile Ser Ser Gly Gly Trp Thr Asn Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Arg
                85                  90                  95

Ala Ala Pro Val Arg Gly Tyr Leu Ile Gly Arg Val Phe Trp Gly Gln
            100                 105                 110

Gly Thr Leu Val Thr Val Lys Pro
        115                 120

<210> SEQ ID NO 44
<211> LENGTH: 121
<212> TYPE: PRT
<213> ORGANISM: Artificial Sequence
<220> FEATURE:
<223> OTHER INFORMATION: chemically synthesized

<400> SEQUENCE: 44

Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Ile Phe Ser Val Asn
            20                  25                  30

Asn Met Gly Trp Tyr Arg Gln Ala Pro Gly Lys Gln Arg Glu Leu Val
        35                  40                  45

Ser Val Ile Thr Val Asn Gly Ile Thr Thr Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Gly Tyr Ile Arg Leu Ala Ala Thr Asn Pro Tyr Val Gly Tyr Trp Gly
            100                 105                 110

Gln Gly Thr Leu Val Thr Val Lys Pro
        115                 120

<210> SEQ ID NO 45
<211> LENGTH: 15
<212> TYPE: PRT
<213> ORGANISM: Artificial Sequence
<220> FEATURE:
<223> OTHER INFORMATION: chemically synthesized

<400> SEQUENCE: 45

Gly Gly Ser Gly Gly Ser Gly Gly Ser Gly Gly Ser Gly Gly Ser
1               5                   10                  15

<210> SEQ ID NO 46
<211> LENGTH: 111
<212> TYPE: PRT

<213> ORGANISM: Artificial Sequence
<220> FEATURE:
<223> OTHER INFORMATION: chemically synthesized

<400> SEQUENCE: 46

Gln Leu Gln Leu Gln Glu Ser Gly Gly Gly Leu Val Gln Ser Gly Arg
1               5                   10                  15

Ser Leu Arg Leu Ser Cys Ser Ala Ser Gly Ser Leu Phe Arg Phe Asp
            20                  25                  30

Thr Val Trp Trp Tyr Arg Gln Ala Pro Gly Lys Gln Arg Glu Trp Val
        35                  40                  45

Ala Tyr Ile Thr Ala Gly Gly Met Thr Asn Tyr Ala Asp Ser Val Lys
50                  55                  60

Gly Arg Phe Thr Ile Ser Lys Asp Asn Ala Lys Asn Met Val Tyr Leu
65                  70                  75                  80

Gln Met Asp Ser Leu Leu Pro Glu Asp Thr Ala Val Tyr Tyr Cys Asn
                85                  90                  95

Val Gly Arg Asn Trp Gly Gln Gly Thr Gln Val Thr Val Ser Ser
            100                 105                 110

<210> SEQ ID NO 47
<211> LENGTH: 112
<212> TYPE: PRT
<213> ORGANISM: Artificial Sequence
<220> FEATURE:
<223> OTHER INFORMATION: chemically synthesized

<400> SEQUENCE: 47

Glu Val Gln Leu Val Gln Ser Gly Gly Gly Leu Val Gln Pro Gly Glu
1               5                   10                  15

Ser Leu Arg Leu Ser Cys Ala Ala Ser Gly Asn Ile Phe Arg Phe Asp
            20                  25                  30

Thr Val Trp Trp Tyr Arg Gln Pro Pro Gly Glu Gln Arg Glu Trp Val
        35                  40                  45

Ser Tyr Ile Thr Ala Gly Ser Ile Thr Asn Tyr Ala Asp Ser Val Lys
50                  55                  60

Gly Arg Phe Thr Ile Ser Arg Asp Asn Ala Lys Asn Met Val Tyr Leu
65                  70                  75                  80

Gln Met Asp Asn Leu Lys Pro Glu Asp Thr Ala Val Tyr Tyr Cys Arg
                85                  90                  95

Val Gly Gly Ser Ser Trp Gly Gln Gly Thr Gln Val Thr Val Ser Ser
            100                 105                 110

<210> SEQ ID NO 48
<211> LENGTH: 120
<212> TYPE: PRT
<213> ORGANISM: Artificial Sequence
<220> FEATURE:
<223> OTHER INFORMATION: chemically synthesized

<400> SEQUENCE: 48

Glu Val Gln Leu Val Gln Ser Gly Gly Gly Leu Val Gln Ala Gly Asp
1               5                   10                  15

Ser Leu Arg Leu Ser Cys Ala Ala Ser Gly Gly Ile Ser Ser Thr Tyr
            20                  25                  30

Ala Met Gly Trp Phe Arg Gln Ala Pro Gly Lys Glu Arg Glu Phe Val
        35                  40                  45

Ala Ser Ile Arg Leu Gly Ser Glu Ala Thr Tyr Tyr Ala Asp Ser Val
50                  55                  60

```
Lys Gly Arg Phe Thr Ile Ser Arg Asp Asn Ala Leu Lys Thr Ile Tyr
 65                  70                  75                  80

Leu Gln Met Asn Ser Leu Lys Pro Asp Asp Thr Ala Val Tyr Tyr Cys
                 85                  90                  95

Ala Val Asp Ala Ser Leu Phe Leu Val Thr Val Asp Tyr Trp Gly Arg
            100                 105                 110

Gly Thr Gln Val Thr Val Ser Ser
        115                 120

<210> SEQ ID NO 49
<211> LENGTH: 125
<212> TYPE: PRT
<213> ORGANISM: Artificial Sequence
<220> FEATURE:
<223> OTHER INFORMATION: chemically synthesized

<400> SEQUENCE: 49

Gln Val Gln Leu Val Gln Ser Gly Gly Gly Leu Val Gln Ala Gly Gly
  1               5                  10                  15

Ser Leu Arg Leu Ser Cys Ala Ala Ser Gly Arg Thr Phe Ser Arg Cys
                 20                  25                  30

Val Met Gly Trp Phe Arg Gln Ala Pro Gly Lys Glu Arg Glu Phe Val
             35                  40                  45

Ala Thr Ile Ser Trp Ser Gly Ala Ser Thr Val Tyr Ala Asp Ser Val
 50                  55                  60

Lys Gly Arg Phe Thr Ile Ser Arg Glu Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Ala Glu Ser Ser Trp Asn Gly Asp Ile Arg Leu Lys Gly Tyr
            100                 105                 110

Asp Tyr Trp Gly Gln Gly Thr Gln Val Thr Val Ser Ser
        115                 120                 125

<210> SEQ ID NO 50
<211> LENGTH: 127
<212> TYPE: PRT
<213> ORGANISM: Artificial Sequence
<220> FEATURE:
<223> OTHER INFORMATION: chemically synthesized

<400> SEQUENCE: 50

Gln Val Thr Leu Lys Glu Ser Gly Gly Gly Leu Val Gln Ala Gly Gly
  1               5                  10                  15

Ser Leu Arg Leu Ser Cys Ala Ala Ser Gly Arg Ser Phe Arg Thr Tyr
                 20                  25                  30

Thr Met Ala Trp Phe Arg Gln Pro Pro Gly Lys Glu Arg Glu Phe Val
             35                  40                  45

Ala Ala Ile Thr Trp Ser Gly Ser Thr Phe Tyr Ala Asp Pro Val
 50                  55                  60

Lys Gly Arg Phe Thr Ile Ser Arg Asp Asn Ala Lys Asn Thr Val Tyr
 65                  70                  75                  80

Leu Gln Met Asn Thr Leu Lys Pro Glu Asp Thr Ala Val Tyr Tyr Cys
                 85                  90                  95

Ala Val Glu Thr Ser Ile Ser Gly Arg Tyr Thr Val Phe Gln Pro Arg
            100                 105                 110

Phe Tyr Asp Ser Trp Gly Gln Gly Thr Gln Val Thr Val Ser Ser
```

```
<210> SEQ ID NO 51
<211> LENGTH: 112
<212> TYPE: PRT
<213> ORGANISM: Artificial Sequence
<220> FEATURE:
<223> OTHER INFORMATION: chemically synthesized

<400> SEQUENCE: 51
```

Gln Val Gln Leu Gln Glu Ser Gly Gly Gly Leu Val Gln Pro Gly Glu
1               5                   10                  15

Ser Leu Arg Leu Ser Cys Ala Ala Ser Gly Asn Ile Phe Arg Phe Asp
            20                  25                  30

Thr Val Trp Trp Tyr Arg Gln Pro Pro Gly Glu Gln Arg Glu Trp Val
        35                  40                  45

Ser Tyr Ile Thr Ala Gly Ser Ile Thr Asn Tyr Ala Asp Ser Val Lys
    50                  55                  60

Gly Arg Phe Ile Ile Ser Arg Asp Asn Ala Lys Asn Met Val Tyr Leu
65                  70                  75                  80

Gln Met Asp Asn Leu Lys Pro Glu Asp Thr Ala Val Tyr Tyr Cys Arg
                85                  90                  95

Val Gly Gly Gly Ser Trp Gly Gln Gly Thr Gln Val Thr Val Ser Ser
            100                 105                 110

```
<210> SEQ ID NO 52
<211> LENGTH: 116
<212> TYPE: PRT
<213> ORGANISM: Artificial Sequence
<220> FEATURE:
<223> OTHER INFORMATION: chemically synthesized

<400> SEQUENCE: 52
```

Glu Val Gln Leu Val Gln Ser Gly Gly Gly Leu Val Gln Pro Gly Gly
1               5                   10                  15

Ser Leu Arg Leu Ser Cys Ile Ala Ser Gly Ser Ile Phe Ser Thr Lys
            20                  25                  30

Thr Met Gly Trp Tyr Arg Gln Ala Pro Gly Lys Gln Arg Glu Trp Val
        35                  40                  45

Ala Leu Ile Thr Thr Gly Leu Ser Thr Gln Tyr Leu Asp Ser Leu Glu
    50                  55                  60

Gly Arg Phe Thr Ile Ser Arg Asp Asn Ala Asn Asn Arg Val Phe Leu
65                  70                  75                  80

Gln Met Asn Asn Leu Lys Pro Glu Asp Thr Gly Val Tyr Tyr Cys Asn
                85                  90                  95

Val Val Pro Gly Arg Gly Ala Thr Tyr Trp Gly Lys Gly Thr Gln Val
            100                 105                 110

Thr Val Ser Ser
        115

```
<210> SEQ ID NO 53
<211> LENGTH: 111
<212> TYPE: PRT
<213> ORGANISM: Artificial Sequence
<220> FEATURE:
<223> OTHER INFORMATION: chemically synthesized

<400> SEQUENCE: 53
```

Gln Leu Gln Leu Gln Glu Ser Gly Gly Gly Leu Val Gln Pro Gly Arg
1               5                   10                  15

Ser Leu Arg Leu Ser Cys Ala Gly Ser Gly Ser Ile Phe Arg Tyr Asp
            20                  25                  30

Thr Val Trp Trp Tyr Arg Gln Ala Pro Gly Lys Gln Arg Glu Trp Val
        35                  40                  45

Ala Tyr Val Thr Ala Gly Gly Ile Thr Asn Tyr Ala Asp Ser Val Lys
 50                  55                  60

Gly Arg Phe Thr Ile Ser Lys Asp Asn Ala Lys Asn Met Val Tyr Leu
 65                  70                  75                  80

Gln Met Asp Ser Leu Leu Pro Glu Asp Thr Ala Val Tyr Tyr Cys His
                85                  90                  95

Val Gly Arg Asn Trp Gly Gln Thr Gln Val Thr Val Ser Ser
            100                 105                 110

<210> SEQ ID NO 54
<211> LENGTH: 121
<212> TYPE: PRT
<213> ORGANISM: Artificial Sequence
<220> FEATURE:
<223> OTHER INFORMATION: chemically synthesized

<400> SEQUENCE: 54

Gln Leu Gln Leu Gln Glu Ser Gly Gly Gly Leu Val Gln Ala Gly Gly
 1               5                  10                  15

Ser Leu Arg Leu Ser Cys Ala Ala Ser Gly Arg Thr Phe Ser Ser Asn
            20                  25                  30

Val Tyr Ser Met Gly Trp Phe Arg Gln Ala Pro Gly Lys Glu Arg Glu
        35                  40                  45

Phe Val Ser Ala Ile Thr Trp Arg Gly Gly Thr Thr Tyr Tyr Ala Asp
 50                  55                  60

Ser Val Lys Asp Arg Phe Thr Ile Ser Lys Asp Asn Ala Lys Asn Thr
 65                  70                  75                  80

Val Tyr Leu Gln Met Asn Ser Leu Lys Ser Glu Asp Thr Ala Val Tyr
                85                  90                  95

Tyr Cys Ala Cys Ser Arg Met Asp Ser Thr Arg Tyr Asp Tyr Trp Gly
            100                 105                 110

Gln Gly Thr Gln Val Thr Val Ser Ser
        115                 120

<210> SEQ ID NO 55
<211> LENGTH: 111
<212> TYPE: PRT
<213> ORGANISM: Artificial Sequence
<220> FEATURE:
<223> OTHER INFORMATION: chemically synthesized

<400> SEQUENCE: 55

Glu Val Gln Leu Val Gln Ser Gly Gly Gly Leu Val Gln Ser Gly Arg
 1               5                  10                  15

Ser Leu Arg Leu Ser Cys Ser Ala Ser Gly Ser Leu Phe Arg Phe Asp
            20                  25                  30

Thr Val Trp Trp Tyr Arg Gln Ala Pro Gly Lys Gln Arg Glu Trp Val
        35                  40                  45

Ala Tyr Ile Thr Ala Gly Gly Ile Thr Asn Tyr Ala Asp Ser Val Lys
 50                  55                  60

Gly Arg Phe Thr Ile Ser Lys Asp Asn Ala Lys Asn Met Val Tyr Leu
 65                  70                  75                  80

Gln Met Asp Ser Leu Leu Pro Glu Asp Thr Ala Val Tyr Tyr Cys Ser 85                  90                  95

Val Gly Arg Asn Trp Gly Gln Gly Thr Gln Val Thr Val Ser Ser
                100                 105                 110

<210> SEQ ID NO 56
<211> LENGTH: 114
<212> TYPE: PRT
<213> ORGANISM: Artificial Sequence
<220> FEATURE:
<223> OTHER INFORMATION: chemically synthesized

<400> SEQUENCE: 56

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ile Thr Val Arg Ile Asn
            20                  25                  30

Thr Met Gly Trp Tyr Arg Gln Ala Pro Gly Lys Gln Arg Glu Leu Val
        35                  40                  45

Ala Tyr Ile Thr Ser Gly Gly Ile Thr Asn Tyr Val Asp Ser Val Lys
    50                  55                  60

Gly Arg Phe Thr Ile Ala Arg Asp Asp Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val His Gly Trp Arg Asp Phe Trp Gly Gln Gly Thr Gln Val Thr Val
                100                 105                 110

Ser Ser

<210> SEQ ID NO 57
<211> LENGTH: 117
<212> TYPE: PRT
<213> ORGANISM: Artificial Sequence
<220> FEATURE:
<223> OTHER INFORMATION: chemically synthesized

<400> SEQUENCE: 57

Gln Val Gln Leu Val Gln Ser Gly Gly Gly Leu Val Gln Pro Gly Gly
1               5                   10                  15

Ser Leu Arg Leu Ser Cys Ala Ala Ser Gly Thr Ile Phe Arg Phe Asn
            20                  25                  30

Thr Met Ala Trp Tyr Arg Gln Ala Pro Gly Lys Gln Arg Glu Phe Val
        35                  40                  45

Ala Tyr Ile Thr Trp Ala Gly Met Thr Gly Tyr Gln Asp Ser Val Gln
    50                  55                  60

Asp Arg Phe Thr Ile Ser Arg Asp Asn Ala Lys Asn Thr Val Ser Leu
65                  70                  75                  80

Gln Met Asn Asn Leu Lys Pro Glu Asp Thr Ala Val Tyr Phe Cys Asn
                85                  90                  95

Lys His Gly Ser Ser Phe Val Arg Asp Tyr Trp Gly Gln Gly Thr Gln
                100                 105                 110

Val Thr Val Ser Ser
        115

<210> SEQ ID NO 58
<211> LENGTH: 117
<212> TYPE: PRT
<213> ORGANISM: Artificial Sequence
<220> FEATURE:
<223> OTHER INFORMATION: chemically synthesized

<400> SEQUENCE: 58

Glu Val Gln Leu Val Gln Ser Gly Gly Gly Leu Val Gln Pro Gly Gly
1               5                   10                  15

Ser Leu Arg Leu Ser Cys Ala Ala Gly Ser Asp Phe Ala Ile Gly
            20                  25                  30

Ala Met Gly Trp Tyr Arg Gln Ala Pro Gly Lys Gln Arg Asp Phe Val
        35                  40                  45

Ala His Ile Thr Ser Gly Gly Ile Pro Ser Phe Ala Asp Ser Val Lys
    50                  55                  60

Gly Arg Phe Thr Leu Ser Arg Asp Asn Ala Lys Asn Thr Val Tyr Leu
65                  70                  75                  80

Gln Met Asp Ser Leu Lys Pro Asp Asp Thr Ala Val Tyr Tyr Cys Tyr
                85                  90                  95

Leu Arg Lys Arg Gly Ser Gly Thr Thr Thr Trp Gly Gln Gly Thr Gln
            100                 105                 110

Val Thr Val Ser Ser
        115

<210> SEQ ID NO 59
<211> LENGTH: 131
<212> TYPE: PRT
<213> ORGANISM: Artificial Sequence
<220> FEATURE:
<223> OTHER INFORMATION: chemically synthesized

<400> SEQUENCE: 59

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Ser Asn Cys
            20                  25                  30

Val Met Gly Trp Phe Arg Gln Ala Pro Gly Lys Glu Arg Glu Phe Val
        35                  40                  45

Ala Ala Ile Ser Trp Ser Gly Asp Thr Thr His Tyr Ala Asp Ser Leu
    50                  55                  60

Lys Gly Arg Phe Ala Ile Ser Arg Asp Asn Ala Asn Asn Thr Val Phe
65                  70                  75                  80

Leu Gln Lys Asp Ser Leu Thr Pro Ser Asp Thr Ala Val Tyr Tyr Cys
                85                  90                  95

Ala Ala Ser Ser Arg Ile Thr Ser Cys Gln Ala Met Gly Val Val Pro
            100                 105                 110

Leu Leu Gln Pro Trp Tyr Asp Tyr Trp Gly Arg Gly Thr Gln Val Thr
        115                 120                 125

Val Ser Ser
    130

<210> SEQ ID NO 60
<211> LENGTH: 111
<212> TYPE: PRT
<213> ORGANISM: Artificial Sequence
<220> FEATURE:
<223> OTHER INFORMATION: chemically synthesized

<400> SEQUENCE: 60

Gln Val Gln Leu Gln Glu Ser Gly Gly Gly Leu Val Gln Pro Gly Arg
1               5                   10                  15

Ser Leu Arg Leu Ser Cys Ala Ala Ser Gly Asn Ile Phe Arg Phe Asp
            20                  25                  30

```
Thr Val Trp Trp Tyr Arg Gln Ala Pro Gly Lys Gln Arg Glu Trp Val
        35                  40                  45

Ala Tyr Val Thr Ala Gly Gly Ile Thr Asn Tyr Ala Asp Ser Val Lys
 50                  55                  60

Gly Arg Phe Thr Ile Ser Lys Asp Asn Ala Lys Asn Ile Val Tyr Leu
65                   70                  75                  80

His Thr Asp Asn Leu Ala Pro Glu Asp Thr Ala Val Tyr Tyr Cys Arg
                85                  90                  95

Val Gly Gln Asn Trp Gly Gln Gly Thr Gln Val Thr Val Ser Ser
            100                 105                 110
```

```
<210> SEQ ID NO 61
<211> LENGTH: 117
<212> TYPE: PRT
<213> ORGANISM: Artificial Sequence
<220> FEATURE:
<223> OTHER INFORMATION: chemically synthesized

<400> SEQUENCE: 61

Gln Leu Gln Leu Gln Glu Ser Gly Gly Gly Leu Val Gln Pro Gly Gly
1               5                   10                  15

Ser Pro Arg Leu Ser Cys Ala Ala Ser Glu Ser Ile Phe Arg Phe Asn
            20                  25                  30

Thr Met Ala Trp Tyr Arg Gln Ala Pro Gly Lys Gln Arg Glu Leu Val
        35                  40                  45

Ala Tyr Ile Thr Trp Ala Gly Arg Thr Asp Tyr Gly Asp Phe Val Lys
 50                  55                  60

Gly Arg Phe Thr Ile Ser Arg Asp Asn Ala Lys Asn Thr Val Ser Leu
65                   70                  75                  80

Gln Met Asn Ser Leu Lys Pro Glu Asp Thr Ala Val Tyr Tyr Cys Asn
                85                  90                  95

Lys His Gly Ser Arg Phe Glu Arg Asp Tyr Trp Gly Gln Gly Thr Gln
            100                 105                 110

Val Thr Val Ser Ser
        115
```

```
<210> SEQ ID NO 62
<211> LENGTH: 117
<212> TYPE: PRT
<213> ORGANISM: Artificial Sequence
<220> FEATURE:
<223> OTHER INFORMATION: chemically synthesized

<400> SEQUENCE: 62

Gln Val Gln Leu Gln Glu Ser Gly Gly Asp Leu Val Gln Pro Gly Gly
1               5                   10                  15

Ser Leu Arg Leu Ser Cys Val Ala Ser Glu Thr Ile Phe Arg Phe Asn
            20                  25                  30

Thr Met Ala Trp Tyr Arg Gln Ala Pro Gly Lys Arg Arg Glu Leu Val
        35                  40                  45

Gly Tyr Ile Thr Trp Ala Gly Arg Thr Gly Tyr Gly Asp Phe Val Glu
 50                  55                  60

Gly Arg Phe Thr Ile Ser Arg Asp Asn Ser Lys Asn Thr Val Ser Leu
65                   70                  75                  80

Gln Met Asn Ser Leu Lys Pro Glu Asp Thr Ala Val Tyr Tyr Cys Asn
                85                  90                  95

Lys His Gly Ser Ser Phe Thr Gln Asp Tyr Trp Gly Gln Gly Thr Gln
```

Val Thr Val Ser Ser
        115

<210> SEQ ID NO 63
<211> LENGTH: 117
<212> TYPE: PRT
<213> ORGANISM: Artificial Sequence
<220> FEATURE:
<223> OTHER INFORMATION: chemically synthesized

<400> SEQUENCE: 63

Gln Leu Gln Leu Gln Glu Ser Gly Gly Asp Leu Val Gln Pro Gly Gly
1               5                   10                  15

Ser Leu Arg Leu Ser Cys Val Ala Ser Glu Thr Ile Phe Arg Phe Asn
            20                  25                  30

Thr Met Ala Trp Tyr Arg Gln Ala Pro Gly Lys Arg Arg Glu Leu Val
        35                  40                  45

Gly Tyr Ile Thr Trp Ala Gly Arg Thr Gly Tyr Gly Asp Phe Val Glu
    50                  55                  60

Gly Arg Phe Thr Val Ser Arg Asp Asn Ser Lys Asn Thr Val Ser Leu
65                  70                  75                  80

Gln Met Asn Ser Leu Lys Pro Glu Asp Thr Ala Val Tyr Tyr Cys Asn
                85                  90                  95

Lys His Gly Ala Ser Phe Thr Gln Asp Tyr Trp Gly Gln Gly Thr Gln
            100                 105                 110

Val Thr Val Ser Ser
        115

<210> SEQ ID NO 64
<211> LENGTH: 117
<212> TYPE: PRT
<213> ORGANISM: Artificial Sequence
<220> FEATURE:
<223> OTHER INFORMATION: chemically synthesized

<400> SEQUENCE: 64

Gln Leu Gln Leu Gln Glu Ser Gly Gly Gly Leu Val Arg Pro Gly Ser
1               5                   10                  15

Ser Leu Thr Leu Ser Cys Val Ala Ser Glu Thr Ile Phe Arg Phe Asn
            20                  25                  30

Thr Met Ala Trp Tyr Arg Gln Ala Pro Gly Lys Arg Arg Glu Leu Val
        35                  40                  45

Gly Tyr Ile Thr Trp Ala Gly Arg Thr Gly Tyr Gly Asp Phe Val Glu
    50                  55                  60

Gly Arg Phe Thr Ile Ser Arg Asp Asn Ser Lys Asn Thr Val Ser Leu
65                  70                  75                  80

Gln Met Asn Ser Leu Glu Pro Glu Asp Thr Ala Asp Tyr Tyr Cys Asn
                85                  90                  95

Lys His Gly Ser Ser Phe Leu Arg Asp Tyr Trp Gly Gln Gly Thr Gln
            100                 105                 110

Val Thr Val Ser Ser
        115

<210> SEQ ID NO 65
<211> LENGTH: 112
<212> TYPE: PRT
<213> ORGANISM: Artificial Sequence
<220> FEATURE:

<223> OTHER INFORMATION: chemically synthesized

<400> SEQUENCE: 65

```
Gln Val Gln Leu Gln Glu Ser Gly Gly Gly Leu Val Gln Pro Gly Arg
1               5                   10                  15

Ser Leu Arg Leu Ser Cys Ala Gly Ser Gly Ser Met Phe Arg Phe Asp
            20                  25                  30

Thr Val Trp Trp Tyr Arg Gln Ala Pro Gly Lys Gln Arg Asp Trp Val
        35                  40                  45

Ser Tyr Ile Thr Ala Gly Ser Ile Ala Asn Tyr Ala Asp Ser Val Lys
    50                  55                  60

Gly Arg Phe Thr Ile Ser Arg Asp Asn Thr Lys Asn Met Val Tyr Leu
65                  70                  75                  80

Gln Met Asp Ser Leu Lys Pro Glu Asp Thr Ala Val Tyr Tyr Cys Arg
                85                  90                  95

Val Gly Gly Asn Ser Trp Gly Gln Gly Thr Gln Val Thr Val Ser Ser
            100                 105                 110
```

<210> SEQ ID NO 66
<211> LENGTH: 117
<212> TYPE: PRT
<213> ORGANISM: Artificial Sequence
<220> FEATURE:
<223> OTHER INFORMATION: chemically synthesized

<400> SEQUENCE: 66

```
Gln Val Gln Leu Gln Gln Ser Gly Gly Gly Leu Val Gln Pro Gly Gly
1               5                   10                  15

Ser Leu Arg Leu Ser Cys Glu Ala Ser Ser Asn Ile Phe Arg Phe Asn
            20                  25                  30

Thr Met Ala Trp Tyr Arg Gln Ala Pro Gly Lys Gln Arg Glu Phe Ala
        35                  40                  45

Ala Tyr Ile Thr Trp Ala Gly Leu Thr Gly Tyr Gly Asp Ser Leu Lys
    50                  55                  60

Gly Arg Phe Ile Ile Ser Arg Asp Asn Ala Lys Asn Ile Val Thr Leu
65                  70                  75                  80

Gln Met Asn Ser Leu Lys Pro Glu Asp Thr Ala Val Tyr Tyr Cys Asn
                85                  90                  95

Lys His Gly Ser Asp Phe Val Arg Asp Tyr Trp Gly Gln Gly Thr Gln
            100                 105                 110

Val Thr Val Ser Ser
        115
```

<210> SEQ ID NO 67
<211> LENGTH: 116
<212> TYPE: PRT
<213> ORGANISM: Artificial Sequence
<220> FEATURE:
<223> OTHER INFORMATION: chemically synthesized

<400> SEQUENCE: 67

```
Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Ile Phe Ser Thr Lys
            20                  25                  30

Thr Met Gly Trp Tyr Arg Gln Ala Pro Gly Lys Gln Arg Glu Trp Val
        35                  40                  45

Ser Leu Ile Thr Thr Gly Leu Ser Thr Gln Tyr Ala Glu Ser Val Lys
```

```
                    50                  55                  60
Gly Arg Phe Thr Ile Ser Arg Asp Asn Ala Asn Asn Thr Val Tyr Leu
 65                  70                  75                  80

Gln Met Ser Ser Leu Arg Ala Glu Asp Thr Ala Val Tyr Tyr Cys Asn
                     85                  90                  95

Val Val Pro Gly Arg Gly Ala Thr Tyr Trp Gly Gln Gly Thr Leu Val
                    100                 105                 110

Thr Val Lys Pro
            115

<210> SEQ ID NO 68
<211> LENGTH: 116
<212> TYPE: PRT
<213> ORGANISM: Artificial Sequence
<220> FEATURE:
<223> OTHER INFORMATION: chemically synthesized

<400> SEQUENCE: 68

Glu Val Gln Leu Leu Glu Ser Gly Gly Gly Val Gln Pro Gly Gly
 1               5                  10                  15

Ser Leu Arg Leu Ser Cys Ala Ala Ser Gly Ser Ile Phe Ser Thr Lys
                 20                  25                  30

Thr Met Gly Trp Tyr Arg Gln Ala Pro Gly Lys Gln Arg Glu Trp Val
             35                  40                  45

Ser Leu Ile Thr Thr Gly Leu Ser Thr Gln Tyr Ala Glu Ser Val Lys
         50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Asn
                     85                  90                  95

Val Val Pro Gly Arg Gly Ala Thr Tyr Trp Gly Gln Gly Thr Leu Val
                    100                 105                 110

Thr Val Lys Pro
            115

<210> SEQ ID NO 69
<211> LENGTH: 116
<212> TYPE: PRT
<213> ORGANISM: Artificial Sequence
<220> FEATURE:
<223> OTHER INFORMATION: chemically synthesized

<400> SEQUENCE: 69

Glu Val Gln Leu Leu Glu Ser Gly Gly Gly Val Gln Pro Gly Gly
 1               5                  10                  15

Ser Leu Arg Leu Ser Cys Ala Ala Ser Gly Ser Ile Phe Ser Thr Lys
                 20                  25                  30

Thr Met Gly Trp Tyr Arg Gln Ala Pro Gly Lys Gly Leu Glu Trp Val
             35                  40                  45

Ser Leu Ile Thr Thr Gly Leu Ser Thr Gln Tyr Ala Glu Ser Val Lys
         50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Asn
                     85                  90                  95

Val Val Pro Gly Arg Gly Ala Thr Tyr Trp Gly Gln Gly Thr Leu Val
                    100                 105                 110
```

Thr Val Lys Pro
        115

<210> SEQ ID NO 70
<211> LENGTH: 116
<212> TYPE: PRT
<213> ORGANISM: Artificial Sequence
<220> FEATURE:
<223> OTHER INFORMATION: chemically synthesized

<400> SEQUENCE: 70

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Ile Phe Ser Thr Lys
            20                  25                  30

Thr Met Gly Trp Tyr Arg Gln Ala Pro Gly Lys Gly Leu Glu Trp Val
        35                  40                  45

Ser Leu Ile Thr Thr Gly Leu Ser Thr Gln Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Asn
                85                  90                  95

Val Val Pro Gly Arg Gly Ala Thr Tyr Trp Gly Gln Gly Thr Leu Val
            100                 105                 110

Thr Val Lys Pro
        115

<210> SEQ ID NO 71
<211> LENGTH: 121
<212> TYPE: PRT
<213> ORGANISM: Artificial Sequence
<220> FEATURE:
<223> OTHER INFORMATION: chemically synthesized

<400> SEQUENCE: 71

Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Ile Phe Ser Val Asn
            20                  25                  30

Asn Met Gly Trp Tyr Arg Gln Ala Pro Gly Lys Gln Arg Glu Leu Val
        35                  40                  45

Ser Val Ile Thr Val Gly Gly Ile Thr Thr Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Gly Tyr Ile Arg Leu Ala Ala Thr Asn Pro Tyr Val Gly Tyr Trp Gly
            100                 105                 110

Gln Gly Thr Leu Val Thr Val Lys Pro
            115                 120

<210> SEQ ID NO 72
<211> LENGTH: 121
<212> TYPE: PRT
<213> ORGANISM: Artificial Sequence
<220> FEATURE:
<223> OTHER INFORMATION: chemically synthesized

```
<400> SEQUENCE: 72

Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Ile Phe Ser Val Asn
            20                  25                  30

Asn Met Gly Trp Tyr Arg Gln Ala Pro Gly Lys Gln Arg Glu Leu Val
        35                  40                  45

Ser Val Ile Thr Val Gln Gly Ile Thr Thr Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Gly Tyr Ile Arg Leu Ala Ala Thr Asn Pro Tyr Val Gln Tyr Trp Gly
            100                 105                 110

Gln Gly Thr Leu Val Thr Val Lys Pro
        115                 120

<210> SEQ ID NO 73
<211> LENGTH: 121
<212> TYPE: PRT
<213> ORGANISM: Artificial Sequence
<220> FEATURE:
<223> OTHER INFORMATION: chemically synthesized

<400> SEQUENCE: 73

Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Ile Phe Ser Val Asn
            20                  25                  30

Asn Met Gly Trp Tyr Arg Gln Ala Pro Gly Lys Gln Arg Glu Leu Val
        35                  40                  45

Ser Val Ile Thr Asn Gln Gly Ile Thr Thr Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Gly Tyr Ile Arg Leu Ala Ala Thr Asn Pro Tyr Val Gln Tyr Trp Gly
            100                 105                 110

Gln Gly Thr Leu Val Thr Val Lys Pro
        115                 120

<210> SEQ ID NO 74
<211> LENGTH: 121
<212> TYPE: PRT
<213> ORGANISM: Artificial Sequence
<220> FEATURE:
<223> OTHER INFORMATION: chemically synthesized

<400> SEQUENCE: 74

Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Ile Phe Ser Val Asn
            20                  25                  30

Asn Met Gly Trp Tyr Arg Gln Ala Pro Gly Lys Gln Arg Glu Leu Val
        35                  40                  45
```

```
Ser Val Ile Thr Val Ser Gly Ile Thr Thr Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                 85                  90                  95

Gly Tyr Ile Arg Leu Ala Ala Thr Asn Pro Tyr Val Gln Tyr Trp Gly
            100                 105                 110

Gln Gly Thr Leu Val Thr Val Lys Pro
        115                 120

<210> SEQ ID NO 75
<211> LENGTH: 6
<212> TYPE: PRT
<213> ORGANISM: Artificial Sequence
<220> FEATURE:
<223> OTHER INFORMATION: chemically synthesized

<400> SEQUENCE: 75

Gly Gly Ser Gly Gly Ser
1               5

<210> SEQ ID NO 76
<211> LENGTH: 9
<212> TYPE: PRT
<213> ORGANISM: Artificial Sequence
<220> FEATURE:
<223> OTHER INFORMATION: chemically synthesized

<400> SEQUENCE: 76

Gly Gly Ser Gly Gly Ser Gly Gly Ser
1               5

<210> SEQ ID NO 77
<211> LENGTH: 12
<212> TYPE: PRT
<213> ORGANISM: Artificial Sequence
<220> FEATURE:
<223> OTHER INFORMATION: chemically synthesized

<400> SEQUENCE: 77

Gly Gly Ser Gly Gly Ser Gly Gly Ser Gly Gly Ser
1               5                   10

<210> SEQ ID NO 78
<211> LENGTH: 5
<212> TYPE: PRT
<213> ORGANISM: Artificial Sequence
<220> FEATURE:
<223> OTHER INFORMATION: chemically synthesized

<400> SEQUENCE: 78

Gly Gly Gly Gly Ser
1               5

<210> SEQ ID NO 79
<211> LENGTH: 10
<212> TYPE: PRT
<213> ORGANISM: Artificial Sequence
<220> FEATURE:
<223> OTHER INFORMATION: chemically synthesized

<400> SEQUENCE: 79

Gly Gly Gly Gly Ser Gly Gly Gly Gly Ser
1               5                   10
```

<210> SEQ ID NO 80
<211> LENGTH: 15
<212> TYPE: PRT
<213> ORGANISM: Artificial Sequence
<220> FEATURE:
<223> OTHER INFORMATION: chemically synthesized

<400> SEQUENCE: 80

Gly Gly Gly Gly Ser Gly Gly Gly Gly Ser Gly Gly Gly Gly Ser
1               5                   10                  15

<210> SEQ ID NO 81
<211> LENGTH: 121
<212> TYPE: PRT
<213> ORGANISM: Artificial Sequence
<220> FEATURE:
<223> OTHER INFORMATION: chemically synthesized

<400> SEQUENCE: 81

Glu Val Gln Leu Leu Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Thr Met Val Trp Tyr Arg Gln Ala Pro Gly Lys Gly Arg Glu Leu Val
        35                  40                  45

Ser Ser Ile Thr Asn Gln Gly Ile Pro His Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Ala Trp Ile Arg Ser Gln Gly Val Ser Pro Tyr Leu Asn Tyr Trp Gly
            100                 105                 110

Gln Gly Thr Leu Val Thr Val Lys Pro
        115                 120

<210> SEQ ID NO 82
<211> LENGTH: 121
<212> TYPE: PRT
<213> ORGANISM: Artificial Sequence
<220> FEATURE:
<223> OTHER INFORMATION: chemically synthesized

<400> SEQUENCE: 82

Glu Val Gln Leu Leu Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Thr Met Val Trp Tyr Arg Gln Ala Pro Gly Lys Gly Leu Glu Leu Val
        35                  40                  45

Ser Ser Ile Thr Asn Gln Gly Ile Pro His Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Ala Trp Ile Arg Ser Gln Gly Val Ser Pro Tyr Leu Asn Tyr Trp Gly
            100                 105                 110

Gln Gly Thr Leu Val Thr Val Lys Pro
        115                 120

<210> SEQ ID NO 83
<211> LENGTH: 120
<212> TYPE: PRT
<213> ORGANISM: Artificial Sequence
<220> FEATURE:
<223> OTHER INFORMATION: chemically synthesized

<400> SEQUENCE: 83

Glu Val Gln Leu Leu Glu Ser Gly Gly Gly Glu Val Gln Pro Gly Gly
1               5                   10                  15

Ser Leu Arg Leu Ser Cys Ala Ala Ser Gly Asn Thr Phe Ser Asp Asn
            20                  25                  30

Ala Met Tyr Trp Tyr Arg Gln Ala Pro Gly Lys Gly Arg Glu Leu Val
        35                  40                  45

Ser Ser Ile Ser Ser Gly Gly Trp Thr Asn Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Arg
                85                  90                  95

Ala Ala Pro Val Arg Gly Tyr Leu Ile Gly Arg Val Phe Trp Gly Gln
            100                 105                 110

Gly Thr Leu Val Thr Val Lys Pro
        115                 120

<210> SEQ ID NO 84
<211> LENGTH: 120
<212> TYPE: PRT
<213> ORGANISM: Artificial Sequence
<220> FEATURE:
<223> OTHER INFORMATION: chemically synthesized

<400> SEQUENCE: 84

Glu Val Gln Leu Leu Glu Ser Gly Gly Gly Glu Val Gln Pro Gly Gly
1               5                   10                  15

Ser Leu Arg Leu Ser Cys Ala Ala Ser Gly Asn Thr Phe Ser Asp Asn
            20                  25                  30

Ala Met Tyr Trp Tyr Arg Gln Ala Pro Gly Lys Gly Leu Glu Leu Val
        35                  40                  45

Ser Ser Ile Ser Ser Gly Gly Trp Thr Asn Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Arg
                85                  90                  95

Ala Ala Pro Val Arg Gly Tyr Leu Ile Gly Arg Val Phe Trp Gly Gln
            100                 105                 110

Gly Thr Leu Val Thr Val Lys Pro
        115                 120

<210> SEQ ID NO 85
<211> LENGTH: 121
<212> TYPE: PRT
<213> ORGANISM: Artificial Sequence
<220> FEATURE:
<223> OTHER INFORMATION: chemically synthesized -continued

<400> SEQUENCE: 85

```
Glu Val Gln Leu Leu Glu Ser Gly Gly Gly Glu Val Gln Pro Gly Gly
1               5                   10                  15
Ser Leu Arg Leu Ser Cys Ala Ala Ser Gly Arg Ile Phe Ser Val Asn
            20                  25                  30
Asn Met Gly Trp Tyr Arg Gln Ala Pro Gly Lys Gly Arg Glu Leu Val
        35                  40                  45
Ser Val Ile Thr Asn Gln Gly Ile Thr Thr Tyr Ala Glu Ser Val Lys
    50                  55                  60
Gly Arg Phe Thr Ile Ser Arg Asp Asn Ala Lys Asn Thr Leu Tyr Leu
65                  70                  75                  80
Gln Met Ser Ser Leu Arg Ala Glu Asp Thr Ala Val Tyr Tyr Cys Tyr
                85                  90                  95
Gly Tyr Ile Arg Leu Ala Ala Thr Asn Pro Tyr Val Gln Tyr Trp Gly
            100                 105                 110
Gln Gly Thr Leu Val Thr Val Lys Pro
        115                 120
```

<210> SEQ ID NO 86
<211> LENGTH: 121
<212> TYPE: PRT
<213> ORGANISM: Artificial Sequence
<220> FEATURE:
<223> OTHER INFORMATION: chemically synthesized

<400> SEQUENCE: 86

```
Glu Val Gln Leu Leu Glu Ser Gly Gly Gly Glu Val Gln Pro Gly Gly
1               5                   10                  15
Ser Leu Arg Leu Ser Cys Ala Ala Ser Gly Arg Ile Phe Ser Val Asn
            20                  25                  30
Asn Met Gly Trp Tyr Arg Gln Ala Pro Gly Lys Gly Leu Glu Leu Val
        35                  40                  45
Ser Val Ile Thr Asn Gln Gly Ile Thr Thr Tyr Ala Glu Ser Val Lys
    50                  55                  60
Gly Arg Phe Thr Ile Ser Arg Asp Asn Ala Lys Asn Thr Leu Tyr Leu
65                  70                  75                  80
Gln Met Ser Ser Leu Arg Ala Glu Asp Thr Ala Val Tyr Tyr Cys Tyr
                85                  90                  95
Gly Tyr Ile Arg Leu Ala Ala Thr Asn Pro Tyr Val Gln Tyr Trp Gly
            100                 105                 110
Gln Gly Thr Leu Val Thr Val Lys Pro
        115                 120
```

<210> SEQ ID NO 87
<211> LENGTH: 121
<212> TYPE: PRT
<213> ORGANISM: Artificial Sequence
<220> FEATURE:
<223> OTHER INFORMATION: chemically synthesized

<400> SEQUENCE: 87

```
Glu Val Gln Leu Leu Glu Ser Gly Gly Gly Glu Val Gln Pro Gly Gly
1               5                   10                  15
Ser Leu Arg Leu Ser Cys Ala Ala Ser Gly Arg Ile Phe Ser Val Asn
            20                  25                  30
Asn Met Gly Trp Tyr Arg Gln Ala Pro Gly Lys Gly Leu Glu Trp Val
        35                  40                  45
```

-continued

```
Ser Val Ile Thr Asn Gln Gly Ile Thr Thr Tyr Ala Glu Ser Val Lys
    50                  55                  60
Gly Arg Phe Thr Ile Ser Arg Asp Asn Ala Lys Asn Thr Leu Tyr Leu
 65                  70                  75                  80
Gln Met Ser Ser Leu Arg Ala Glu Asp Thr Ala Val Tyr Tyr Cys Tyr
                 85                  90                  95
Gly Tyr Ile Arg Leu Ala Ala Thr Asn Pro Tyr Val Gln Tyr Trp Gly
            100                 105                 110
Gln Gly Thr Leu Val Thr Val Lys Pro
        115                 120

<210> SEQ ID NO 88
<211> LENGTH: 116
<212> TYPE: PRT
<213> ORGANISM: Artificial Sequence
<220> FEATURE:
<223> OTHER INFORMATION: chemically synthesized

<400> SEQUENCE: 88

Glu Val Gln Leu Leu Glu Ser Gly Gly Gly Val Gln Pro Gly Gly
 1               5                  10                  15
Ser Leu Arg Leu Ser Cys Ala Ala Ser Gly Ser Ile Phe Ser Thr Lys
             20                  25                  30
Thr Met Gly Trp Tyr Arg Gln Ala Pro Gly Lys Gly Arg Glu Trp Val
             35                  40                  45
Ser Leu Ile Thr Thr Gly Leu Ser Thr Gln Tyr Ala Glu Ser Val Lys
    50                  55                  60
Gly Arg Phe Thr Ile Ser Arg Asp Asn Ala Lys Asn Thr Leu Tyr Leu
 65                  70                  75                  80
Gln Met Ser Ser Leu Arg Ala Glu Asp Thr Ala Val Tyr Tyr Cys Asn
                 85                  90                  95
Val Val Pro Gly Arg Gly Ala Thr Tyr Trp Gly Gln Gly Thr Leu Val
            100                 105                 110
Thr Val Lys Pro
        115
```

TYPE III SECRETION SYSTEM TARGETING MOLECULES

RELATED APPLICATIONS

This application claims the benefit of U.S. Provisional Application No. 62/155,967, filed May 1, 2015 and U.S. Provisional Application No. 62/254,992, filed Nov. 13, 2015; the contents of each of which are incorporated herein by reference in their entirety.

FIELD OF THE INVENTION

This invention relates generally to molecules that specifically bind bacterial V-tip proteins of the type III secretion system of Gram negative bacteria such as PcrV from *Pseudomonas aeruginosa*. More specifically, this invention relates to molecules that block or otherwise inhibit the injection of effector molecules into target cells. The molecules of the present invention are monospecific or multispecific and can bind their target antigen(s) in a monovalent or multivalent manner. In some embodiments, these antibodies may be combined with a bacterial surface targeting component, binding to the *Pseudomonas* protein, OprI. The invention also relates generally to molecules that specifically bind bacterial cell surface proteins such as OprI, and to methods of use these molecules in a variety of therapeutic, diagnostic, and/or prophylactic indications.

BACKGROUND OF THE INVENTION

V-tip proteins of *Pseudomonas aeruginosa* (PcrV) are essential components of the bacterial type III secretion system (T3SS) that is capable of injecting toxic effector molecules into eukaryotic cells. The V-tip proteins are localized at the extreme end of the T3SS apparatus and oligomerization is thought to be necessary for the functional translocalization of the effector molecules across target cell membranes.

OprI is an outer membrane lipoprotein in *Pseudomonas aeruginosa* and other *Pseudomonas* species. OprI is highly conserved in *P. aeruginosa* strains and therefore represents an excellent candidate for cell-surface targeting of *Pseudomonas* bacteria.

Accordingly, there exists a need for compositions and therapies that target V-tip proteins of Gram negative bacteria and cell-surface components such as OprI.

SUMMARY OF THE INVENTION

The disclosure provides molecules, e.g., polypeptides including antibodies, antigen-binding antibody fragments, antibody-like polypeptides, and/or fusion polypeptides, and compositions that bind bacterial V-tip proteins of the type III secretion system of Gram negative bacteria, such as PcrV from *Pseudomonas aeruginosa*, and/or cell-surface proteins such as the OprI protein of *Pseudomonas aeruginosa*, and methods of making and using these compositions in a variety of therapeutic, diagnostic, and/or prophylactic indications. The V-tip protein targeting molecules of the present invention are monospecific or multispecific and can bind their target antigen(s) in a monovalent or multivalent manner.

These molecules are useful in binding and neutralizing or otherwise inhibiting at least one biological activity of one or more bacterial V-tip proteins of the type III secretion system of Gram negative bacteria.

*Pseudomonas aeruginosa* and other drug resistant Gram negative bacteria are a major health concern, causing community acquired and nosocomial infections. Infections with such bacteria can be serious and life-threatening. An important virulence factor is the type 3 secretion system (T3SS). The T3SS of Gram negative bacteria is responsible for translocation of toxins into eukaryotic cells, causing cell death and lysis, thereby allowing the bacterium to establish infection.

PcrV of *Pseudomonas aeruginosa*, is an example of a V-tip protein common to many Gram negative bacterial T3SSs. The V-tip protein is located at the extreme end of the T3SS apparatus and oligomerization is thought to be necessary for the functional translocalization of the effector molecules across target cell membranes. PcrV of *P. aeruginosa* is required for injection of effector molecules (ExoS, ExoT, ExoU, and ExoY) into the eukaryotic cell cytosol, resulting in cell death and lysis. PcrV of *P. aeruginosa* has been shown to be a protective antigen, suggesting that targeting the V-tip proteins of numerous Gram negative bacteria will provide an effective therapeutic option.

In some embodiments, the V-tip protein targeting molecules are antibodies and antibody-like molecules that specifically bind Gram negative bacterial V-tip proteins of the type 3 secretion system (T3SS) apparatus and block the cytotoxicity toward eukaryotic cells. In some embodiments, the V-tip protein targeting antibody, referred to as the V-tip protein binding proteins (VPBP) are derived from antibodies or antigen-binding antibody fragments including, for example, single-chain variable fragments (scFv), Fab fragments, single domain antibodies (sdAb), $V_{NAR}$, or VHHs. In preferred embodiments, the VPBPs are human or humanized sdAb. The sdAb fragments can be derived from VHH, $V_{NAR}$, engineered VH or VK domains. VHHs can be generated from camelid heavy chain only antibodies. $V_{NAR}$s can be generated from cartilaginous fish heavy chain only antibodies. Various methods have been implemented to generate monomeric sdAbs from conventionally heterodimeric VH and VK domains, including interface engineering and selection of specific germline families.

In other embodiments, the VPBPs are derived from non-antibody scaffold proteins for example but not limited to designed ankyrin repeat proteins (darpins), avimer, anticalin/lipocalins, centyrins and fynomers.

In preferred embodiments, the V-tip protein is or is derived from the *Pseudomonas aeruginosa* PcrV, and the VPBP specifically binds PcrV. In some embodiments, the VPBP is able to bind 2 or more VPBPs of various Gram negative bacteria, including at least PcrV from *Pseudomonas aeruginosa*. In some embodiments, the VPBP binds to a V-tip protein from a single Gram negative bacterial species such as PcrV from *Pseudomonas aeruginosa*. In some embodiments, the VPBP binds to a V-tip protein from more than one Gram negative bacterial species, including at least PcrV from *Pseudomonas aeruginosa*, and is thereby considered species cross-reactive.

In some embodiments, the V-tip protein targeting molecule is a fusion protein. Unexpectedly, it was discovered that enhancing the valency of the VPBP greatly enhanced the efficacy of cyto-protection from *Pseudomonas aeruginosa* both in vitro and in vivo. More surprisingly, it was found that targeting two distinct epitopes on PcrV with the distinct VPBPs in a single multispecific fusion protein resulted in an even greater protection from cytotoxicity caused by *Pseudomonas aeruginosa*. The later finding held true, even when the individual monospecific VPBP was only weakly protective. In fact, it was found that when VPBP recognizing distinct epitopes on PCRV were incorporated into a single fusion protein, they were more potent at cyto-protection compared to VPBP-containing fusion proteins that were multivalent to the same epitope on PCRV or to the combination to two separate monospecific VPBP-containing fusion proteins each recognizing a distinct epitope on PCRV.

In some embodiments, the present invention includes fusion proteins incorporating more than one VPBP and are referred to herein as multivalent. In some embodiments, the VPBPs of the fusion protein recognize the same epitope on the target V-protein and are referred to herein as monospecific-multivalent. In other embodiments, the VPBPs of the fusion protein recognize distinct epitopes on the target V-protein and are referred to herein as multispecific-multivalent. In some embodiments, the VPBP-containing fusion protein includes two VPBPs and has a bivalent binding capacity toward the target V-tip protein. In some embodiments, the VPBP-containing fusion protein includes three VPBPs and has a trivalent binding capacity toward the target V-tip protein. In some embodiments, the VPBP-containing fusion protein includes four VPBPs and has a tetravalent binding capacity toward the target V-tip protein. In some embodiments, the VPBP-containing fusion protein includes six VPBPs and has a hexavalent binding capacity toward the target V-tip protein. In some embodiments, the VPBP-containing fusion protein includes eight VPBPs and has an octavalent binding capacity toward the target V-tip protein. In these embodiments, the VPBPs incorporated into the fusion protein of the present invention can be monospecific or multispecific.

Generally the fusion proteins of the present invention consist of at least two or more VPBPs operably linked via a linker polypeptide. The utilization of sdAb fragments as the specific VPBP within the fusion the present invention has the benefit of avoiding the heavy chain: light chain mispairing problem common to many bi/multispecific antibody approaches. In addition, the fusion proteins of the present invention avoid the use of long linkers necessitated by many bispecific antibodies. Furthermore, the fusion proteins of the present invention are generally smaller in size (ranging approximately from 75 to 125 kDa) than a conventional antibody. This reduced molecular weight maybe enable better penetration into site of infection compared to conventional antibodies.

In some embodiments, the fusion protein of the present invention is composed of a single polypeptide. In other embodiments, the fusion protein of the present invention is composed of more than one polypeptide. For example, wherein a heterodimerization domain is incorporated into the fusion protein so as the construct an asymmetric fusion protein. For example if an immunoglobulin Fc region is incorporated into the fusion protein the CH3 domain can be used as homodimerization domain, or the CH3 dimer interface region can be mutated so as to enable heterodimerization.

In some embodiments, the fusion protein contains the VPBPs on opposite ends. For example the VPBPs are located on both the amino-terminal (N-terminal) portion of the fusion protein and the carboxy-terminal (C-terminal) portion of the fusion protein. In other embodiments, all the VPBPs reside on the same end of the fusion protein. For example, VPBPs reside on either the amino or carboxyl terminal portions of the fusion protein.

In some embodiments, the fusion protein lacks an Fc region.

In some embodiments, the fusion protein contains an immunoglobulin Fc region. In some embodiments, the immunoglobulin Fc region is an IgG isotype selected from the group consisting of IgG1 subclass, IgG2 subclass, IgG3 subclass, and IgG4 subclass.

In some embodiments, the immunoglobulin Fc region or immunologically active fragment thereof is an IgG isotype. For example, the immunoglobulin Fc region of the fusion protein is of human IgG1 subclass, having an amino acid sequence:

(SEQ ID NO: 1)
PAPELLGGPS VFLFPPKPKD TLMISRTPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSRDELT KNQVSLTCLV KGFYPSDIAV EWESNGQPEN

NYKTTPPVLD SDGSFFLYSK LTVDKSRWQQ GNVFSCSVMH

EALHNHYTQK SLSLSPGK

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 1.

In some embodiments, the human IgG1 Fc region is modified at amino acid Asn297 (Boxed, Kabat Numbering) to prevent glycosylation of the fusion protein, e.g., Asn297Ala (N297A) or Asn297Asp (N297D). In some embodiments, the Fc region of the fusion protein is modified at amino acid Leu235 (Boxed, Kabat Numbering) to alter Fc receptor interactions, e.g., Leu235Glu (L235E) or Leu235Ala (L235A). In some embodiments, the Fc region of the fusion protein is modified at amino acid Leu234 (Boxed, Kabat Numbering) to alter Fc receptor interactions, e.g., Leu234Ala (L234A). In some embodiments, the Fc region of the fusion protein is altered at both amino acid 234 and 235, e.g., Leu234Ala and Leu235Ala (L234A/L235A) or Leu234Val and Leu235Ala (L234V/L235A). In some embodiments, the Fc region of the fusion protein is lacking an amino acid at one or more of the following positions to reduce Fc receptor binding: Glu233 (E233, Bold in SEQ ID NO: 1), Leu234 (L234), or Leu235 (L235). In some embodiments, the Fc region of the fusion protein is altered at Gly235 to reduce Fc receptor binding. For example, wherein Gly235 is deleted from the fusion protein. In some embodiments, the human IgG1 Fc region is modified at amino acid Gly236 to enhance the interaction with CD32A, e.g., Gly236Ala (G236A, Boxed in SEQ ID NO: 1). In some embodiments, the human IgG1 Fc region is lacks Lys447, which corresponds to residue 218 of SEQ ID NO: 1 (EU index of Kabat et at 1991 *Sequences of Proteins of Immunological Interest*).

In some embodiments, the immunoglobulin Fc region or immunologically active fragment of the fusion protein is of human IgG2 subclass, having an amino acid sequence:

(SEQ ID NO: 2)
PAPPVAGPSV FLFPPKPKDT LMISRTPEVT CVVVDVSHED

PEVQFNWYVD GVEVHNAKTK PREEQFNSTF RVVSVLTVVH

```
QDWLNGKEYK CKVSNKGLPA PIEKTISKTK GQPREPQVYT

LPPSREEMTK NQVSLTCLVK GFYPSDISVE WESNGQPENN

YKTTPPMLDS DGSFFLYSKL TVDKSRWQQG NVFSCSVMHE

ALHNHYTQKS LSLSPGK
```

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 2.

In some embodiments, the human IgG2 Fc region is modified at amino acid Asn297 (Boxed, to prevent to glycosylation of the antibody, e.g., Asn297Ala (N297A) or Asn297Asp (N297D). In some embodiments, the human IgG2 Fc region lacks Lys447, which corresponds to residue 217 of SEQ ID NO: 2 (EU index of Kabat et at 1991 *Sequences of Proteins of Immunological Interest*).

In some embodiments, the immunoglobulin Fc region or immunologically active fragment of the fusion protein is of human IgG3 subclass, having an amino acid sequence:

```
                                              (SEQ ID NO: 3)
PAPELLGGPS VFLFPPKPKD TLMISRTPEV TCVVVDVSHE

DPEVQFKWYV DGVEVHNAKT KPREEQYNST FRVVSVLTVL

HQDWLNGKEY KCKVSNKALP APIEKTISKT KGQPREPQVY

TLPPSREEMT KNQVSLTCLV KGFYPSDIAV EWESSGQPEN

NYNTTPPMLD SDGSFFLYSK LTVDKSRWQQ GNIFSCSVMH

EALHNRFTQK SLSLSPGK
```

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 3.

In some embodiments, the human IgG3 Fc region is modified at amino acid Asn297 (Boxed, Kabat Numbering) to prevent to glycosylation of the antibody, e.g., Asn297Ala (N297A) or Asn297Asp (N297D). In some embodiments, the human IgG3 Fc region is modified at amino acid 435 to extend the half-life, e.g., Arg435His (R435H, boxed in SEQ ID NO: 3). In some embodiments, the human IgG3 Fc region is lacks Lys447, which corresponds to residue 218 of SEQ ID NO: 3 (EU index of Kabat et at 1991 *Sequences of Proteins of Immunological Interest*).

In some embodiments, the immunoglobulin Fc region or immunologically active fragment of the fusion protein is of human IgG4 subclass, having an amino acid sequence:

```
                                              (SEQ ID NO: 4)
PAPEFLGGPS VFLFPPKPKD TLMISRTPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 4.

In other embodiments, the human IgG4 Fc region is modified at amino acid 235 to alter Fc receptor interactions, e.g., Leu235Glu (L235E). In some embodiments, the human IgG4 Fc region is modified at amino acid Asn297 (Kabat Numbering) to prevent to glycosylation of the antibody, e.g., Asn297Ala (N297A) or Asn297Asp (N297D). In some embodiments, the human IgG4 Fc region is lacks Lys447, which corresponds to residue 218 of SEQ ID NO: 4 (EU index of Kabat et at 1991 *Sequences of Proteins of Immunological Interest*).

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et at 2006, *J. Biol Chem* Vol 281(33) 23514-23524), Met428Leu and Asn434Ser (M428L, N434S) (Zalevsky et at 2010 *Nature Biotech*, Vol 28(2) 157-159), Met252Ile, Thr256Asp, Met428Leu (M252I, T256D, M428L, respectively) or Met252Tyr, Met428Leu/Val (M252Y, M428L/V, respectively), (EU index of Kabat et at 1991 *Sequences of Proteins of Immunological Interest*). Met252 corresponds to residue 23 in SEQ ID NOs: 1, 3, and 4 and residue 22 in SEQ ID NO: 2. Ser254 corresponds to corresponds to residue 25 in SEQ ID NOs: 1, 3, and 4 and residue 24 in SEQ ID NO: 2. Thr256 corresponds to residue 27 in SEQ ID NOs: 1, 3, and 4 and residue 26 in SEQ ID NO: 2. Met428 corresponds to residue 199 in SEQ ID NOs: 1, 3, and 4 and residue 198 in SEQ ID NO: 2. Asn434 corresponds to residue 205 in SEQ ID NOs: 1, 3, and 4 and residue 204 in SEQ ID NO: 2.

In some embodiments, where the fusion protein of the invention includes an Fc polypeptide, the Fc polypeptide is mutated or modified. In these embodiments, the mutated or modified Fc polypeptide includes the following mutations: Met252Tyr and Met428Leu (M252Y, M428L) using the Kabat numbering system.

In some embodiments, the human IgG Fc region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11. Examples of mutations that enhance ADCC include modification at Ser239 and Ile332, for example Ser239Asp and Ile332Glu (S239D, I332E). Examples of mutations that enhance CDC include modifications at Lys326 which corresponds to residue 97 of SEQ ID NOs: 1, 3, and 4 and residue 96 of SEQ ID NO: 2, and Glu333, which corresponds to residue 104 of SEQ ID NOs: 1, 3, and 4 and residue 103 of SEQ ID NO: 2. In some embodiments, the Fc region is modified at one or both of these positions, for example Lys326Ala and/or Glu333Ala (K326A and E333A) using the Kabat numbering system.

In some embodiments, the human IgG Fc region is modified to induce heterodimerization. For example, having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, which corresponds to residue 137 of SEQ ID NOs: 1, 3, and 4 and residue 136 of SEQ ID NO: 2, Leu368, which corresponds to residue 139 of SEQ ID NOs: 1, 3, and 4 and residue 138 of SEQ ID NO: 2, and Tyr407, which corresponds to residue 178 of SEQ ID NOs: 1, 3, and 4 and residue 177 of SEQ ID NO: 2, e.g., Ser, Ala and Val, respectively (T366S/L368A/Y407V). Heterodimerization via CH3 modifications can be further stabilized by the introduction of a disulfide bond, for example by changing Ser354, which corresponds to residue 125 of SEQ ID NOs: 1, 3, and 4 and residue 124 of SEQ ID NO: 2, to Cys (S354C) and Y349, which corresponds to residue 120 of SEQ ID NOs: 1, 3, and 4 and residue 119 of SEQ ID NO: 2, to Cys (Y349C) on opposite CH3 domains (Reviewed in Carter, 2001 Journal of Immunological Methods, 248: 7-15). In some of these embodiments, the Fc region may be modified at the protein-A binding site on one member of the heterodimer so as to prevent protein-A binding and thereby enable more efficient purification of the heterodimeric fusion protein. An exemplary modification within this binding site is Ile253, which corresponds to residue 24 of SEQ ID NOs: 1, 3, and 4 and residue 23 of SEQ ID NO: 2, for example Ile253Arg (I253R). For example the I253R modification maybe combined with either the T366S/L368A/Y407V modifications or with the T366W modifications. The T366S/L368A/Y407V modified Fc is capable of forming homodimers as there is no steric occlusion of the dimerization interface as there is in the case of the T336W modified Fc. Therefore, in preferred embodiments the I253R modification is combined with the T366S/L368A/Y407V modified Fc to disallow purification any homodimeric Fc that may have formed.

In some embodiments, the human IgG Fc region is modified to prevent dimerization. In these embodiments, the fusion proteins of the present invention are monomeric. For example modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the fusion protein contains a polypeptide derived from an immunoglobulin hinge region. The hinge region can be selected from any of the human IgG subclasses. For example the fusion protein may contain a modified IgG1 hinge having the sequence of EPKSSDKTHTCPPC (SEQ ID NO: 5), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 6). In some embodiments, the fusion protein has a modified hinge from IgG4, which is modified to prevent or reduce strand exchange, e.g., Ser228Pro (S228P), having the sequence ESKYGPPCPPC (SEQ ID NO: 7). In some embodiments, the fusion protein contains one or more linker polypeptides. In other embodiments, the fusion protein contains one or more linker and one or more hinge polypeptides.

In some embodiments, the fusion proteins of the present invention lack or have reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine, 2-deoxy-fucose, 2-flurofucose; the use of production cell lines with naturally reduced fucosylation pathways, and metabolic engineering of the production cell line.

In some embodiments, the VPBP is engineered to eliminate recognition by pre-existing antibodies found in humans. In some embodiments, single domain antibodies of the present invention are modified by mutation of position Leu11, for example Leu11Glu (L11E) or Leu11Lys (L11K). In other embodiments, single domain antibodies of the present invention are modified by changes in carboxy-terminal region, for example the terminal sequence consists of GQGTLVTVKPGG (SEQ ID NO: 8) or GQGTLVTVEPGG (SEQ ID NO: 9) or modification thereof. In some embodiments, the single domain antibodies of the present invention are modified by mutation of position 11 and by changes in carboxy-terminal region.

In some embodiments, the VPBPs of the fusion proteins of the present invention are operably linked via amino acid linkers. In some embodiments, these linkers are composed predominately of the amino acids Glycine and Serine, denoted as GS-linkers herein. The GS-linkers of the fusion proteins of the present invention can be of various lengths, for example 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., $(GGS)_2$ (SEQ ID NO: 75); GGSGGSGGS, i.e., $(GGS)_3$ (SEQ ID NO: 76); GGSGGSGGSGGS, i.e., $(GGS)_4$ (SEQ ID NO: 77); GGSGGSGGSGGSGGS, i.e., $(GGS)_5$ (SEQ ID NO: 45), GGGGS (SEQ ID NO: 78); GGGGSGGGGS, i.e., $(GGGGS_2)$ (SEQ ID NO: 79), and GGGGSGGGGSGGGGS, i.e., $(GGGGS_3)$ (SEQ ID NO: 80).

In some embodiments, the fusion protein is tetravalent. In some embodiments, the tetravalent fusion protein has the following structure: VHH-Linker-VHH-Linker-Hinge-Fc, where the VHH is a humanized or fully human VHH sequence. In some embodiments, the tetravalent fusion protein has the following structure: VHH-Linker-Hinge-Fc-Linker-VHH, where the VHH is a humanized or fully human VHH sequence.

In some embodiments, the fusion protein is hexavalent. In some embodiments, the hexavalent fusion protein has the following structure: VHH-Linker-VHH-Linker-VHH-Linker-Hinge-Fc, where the VHH is a humanized or fully human VHH sequence. In some embodiments, the hexavalent fusion protein has the following structure: VHH-Linker-VHH-Linker-Hinge-Fc-Linker-VHH, or VHH-Linker-Hinge-Fc-Linker-VHH-Linker-VHH where the VHH is a humanized or fully human VHH sequence.

In some embodiments, the fusion protein lacks an Fc region. In these embodiments, wherein the fusion protein is tetravalent, the protein has the following structure VHH-Linker-VHH-Linker-VHH-Linker-VHH-Linker. In these embodiments, wherein the fusion protein is pentavalent, the protein has the following structure VHH-Linker-VHH-Linker-VHH-Linker-VHH-Linker-VHH. In these embodiments, wherein the fusion protein is hexavalent, the protein has the following structure VHH-Linker-VHH-Linker-VHH-Linker-VHH-Linker-VHH-Linker-VHH. In these embodiments, the VHH is a humanized or fully human VHH sequence.

In some embodiments, the VPBP-containing fusion protein may also contain additional binding domains that recognize non-V-tip proteins of gram negative bacteria such as PcrV from *Pseudomonas aeruginosa*. These additional bacterial binding domains may confer additional functionality to the fusion protein of the present invention. These additional functionalities may include neutralization of additional bacterial virulence or growth factors or enable opsono-phagocytosis of the bacteria by host phagocytic cells. In some embodiments, the VPBP-containing fusion protein may also contain additional binding domains that recognize non-bacterial proteins. These additional non-bacterial binding domains, may confer additional functionality to the fusion protein of the present invention. These additional functionalities may enhance immune cell recruitment or activation, including neutrophils, natural killer cells, macrophages, monocytes, dendritic cells and T-cells.

In some embodiments, the VPBP-containing fusion protein may also contain additional binding domains that recognize the outer membrane protein I (OprI) protein or a fragment thereof. In a preferred embodiment, the VPBP-containing fusion protein includes at least a first domain that binds PcrV or a fragment thereof and a second domain that binds OprI or a fragment thereof. These bispecific fusion proteins are referred to herein as "PcrV×OprI bispecific fusion proteins," "PcrV×OprI fusion proteins" and/or "PcrV×OprI fusions." OprI is a cell surface protein that is highly conserved amongst *P. aeruginosa* strains. OprI is anchored to outer membrane via N-term Cys-lipidation, is present in 100% of *P. aeruginosa* strains tested, and is 100% conserved in genome sequenced *P. aeruginosa* strains.

In some embodiments, the first domain comprises one or more sequences from the PcrV sequences shown in Table 1. In some embodiments, the second domain comprises one or more sequences that bind OprI. In some embodiments, the second domain comprises one or more sequences from the OprI sequences shown in Table 2.

Dual targeting of PcrV and OprI allows the fusion polypeptides to tether or otherwise attach and/or bind to the bacteria cell surface, and it provides enhanced protection in vivo.

In some embodiments, the V-tip protein targeting molecule comprises one or more sequences from the PcrV sequences shown in Table 1.

The molecules provided herein exhibit inhibitory activity, for example by inhibiting at least one biological activity of one or more V-tip proteins of Gram negative bacteria, such as for example, functional translocalization of the effector molecules across target cell membranes. The molecules provided herein completely or partially reduce or otherwise modulate expression or activity of one or more V-tip proteins of Gram negative bacteria upon binding to, or otherwise interacting with, the V-tip protein(s) such as PcrV from *Pseudomonas aeruginosa*. The reduction or modulation of a biological function of one or more V-tip proteins of Gram negative bacteria is complete or partial upon interaction between the molecules and the V-tip protein(s). The molecules are considered to completely inhibit expression or activity of one or more V-tip proteins of Gram negative bacteria when the level of expression or activity of the V-tip protein(s) in the presence of the molecule is decreased by at least 95%, e.g., by 96%, 97%, 98%, 99% or 100% as compared to the level of expression or activity of the V-tip protein(s) in the absence of interaction, e.g., binding, with a molecule described herein. The molecules are considered to partially inhibit expression or activity one or more V-tip proteins of Gram negative bacteria when the level of expression or activity of the V-tip protein(s) in the presence of the molecule is decreased by less than 95%, e.g., 10%, 20%, 25%, 30%, 40%, 50%, 60%, 75%, 80%, 85% or 90% as compared to the level of expression or activity of the V-tip protein(s) in the absence of interaction, e.g., binding, with a molecule described herein.

The V-tip protein targeting molecules provided herein are useful in treating, alleviating a symptom of, ameliorating and/or delaying the progression of a disease or disorder in a subject suffering from or identified as being at risk for a disease or disorder associated with at least one biological activity of one or more V-tip proteins of Gram negative bacteria such as PcrV from *Pseudomonas aeruginosa*, such as, for example, functional translocalization of the effector molecules across target cell membranes.

The disclosure provides molecules, e.g., polypeptides including antibodies, antigen-binding antibody fragments, antibody-like polypeptides, and/or fusion polypeptides, and compositions that bind bacterial non-V-tip proteins of the type III secretion system of Gram negative bacteria, such as OprI from *Pseudomonas aeruginosa*, and methods of making and using these compositions in a variety of therapeutic, diagnostic, and/or prophylactic indications. The OprI-targeting molecules of the present invention are monospecific or multispecific and can bind their target antigen(s) in a monovalent or multivalent manner.

In some embodiments, the OprI-protein targeting molecules are antibodies and antibody-like molecules that specifically bind OprI. In some embodiments, the antibody or antigen-binding fragment thereof are derived from antibodies or antigen-binding antibody fragments including, for example, single-chain variable fragments (scFv), Fab fragments, single domain antibodies (sdAb), $V_{NAR}$, or VHHs. In some embodiments, the anti-OprI antibodies are human or humanized sdAb. The sdAb fragments can be derived from VHH, $V_{NAR}$, engineered VH or VK domains. VHHs can be generated from camelid heavy chain only antibodies. $V_{NAR}$s can be generated from cartilaginous fish heavy chain only antibodies. Various methods have been implemented to generate monomeric sdAbs from conventionally heterodimeric VH and VK domains, including interface engineering and selection of specific germline families.

In other embodiments, the anti-OprI targeting molecules are derived from non-antibody scaffold proteins for example but not limited to designed ankyrin repeat proteins (darpins), avimer, anticalin/lipocalins, centyrins and fynomers.

In some embodiments, the anti-OprI targeting molecule is an antibody or antigen-binding fragment thereof comprising an amino acid sequence selected from the group consisting of SEQ ID NOs: 46-70 and 88. In some embodiments, the anti-OprI targeting antibody or antigen-binding fragment thereof also comprises an immunoglobulin Fc region or immunologically active fragment thereof. In some embodiments, the anti-OprI targeting antibody or antigen-binding fragment thereof also comprises an immunoglobulin Fc region or immunologically active fragment thereof comprising an amino acid sequence selected from the group consisting of SEQ ID NOs: 1-4.

In some embodiments, the fusion protein of the present invention is composed of a single polypeptide. In other embodiments, the fusion protein of the present invention is composed of more than one polypeptide. For example, wherein a heterodimerization domain is incorporated into the fusion protein so as the construct an asymmetric fusion protein. For example if an immunoglobulin Fc region is incorporated into the fusion protein the CH3 domain can be used as homodimerization domain, or the CH3 dimer interface region can be mutated so as to enable heterodimerization.

In some embodiments, the fusion protein contains the VPBPs on opposite ends. For example the VPBPs are located on both the amino-terminal (N-terminal) portion of the fusion protein and the carboxy-terminal (C-terminal) portion of the fusion protein. In other embodiments, all the VPBPs reside on the same end of the fusion protein. For example, VPBPs reside on either the amino or carboxyl terminal portions of the fusion protein.

In some embodiments, the present invention includes fusion proteins incorporating more than one OprI targeting sequence and are referred to herein as multivalent. In some embodiments, the OprI targeting sequences of the fusion protein recognize the same epitope on OprI and are referred to herein as monospecific-multivalent. In other embodiments, the OprI targeting sequences of the fusion protein recognize distinct epitopes on OprI and are referred to herein as multispecific-multivalent. In some embodiments, the OprI targeting sequence-containing fusion protein includes two OprI targeting sequences and has a bivalent binding capacity toward the OprI. In some embodiments, the OprI targeting sequence-containing fusion protein includes three OprI targeting sequences and has a trivalent binding capacity toward the OprI. In some embodiments, the OprI targeting sequence-containing fusion protein includes four OprI targeting sequences and has a tetravalent binding capacity toward the OprI. In some embodiments, the OprI targeting sequence-containing fusion protein includes six OprI targeting sequences and has a hexavalent binding capacity toward the OprI. In some embodiments, the OprI targeting sequence-containing fusion protein includes eight OprI targeting sequences and has an octavalent binding capacity toward the OprI. In these embodiments, the OprI targeting sequences incorporated into the fusion protein of the present invention can be monospecific or multispecific.

In some embodiments, the fusion protein lacks an Fc region.

In some embodiments, the fusion protein comprises an immunoglobulin Fc region or immunologically active fragment thereof comprising an amino acid sequence selected from the group consisting of SEQ ID NOs: 1-4.

In some embodiments, the Fc region of the OprI targeting antibody or antigen-binding fragment thereof or the OprI-targeting fusion polypeptide includes a human IgG1 region. In some embodiments, human IgG1 Fc region is modified at amino acid Asn297 (Boxed, Kabat Numbering) to prevent glycosylation of the antibody and/or fusion protein, e.g., Asn297Ala (N297A) or Asn297Asp (N297D). In some embodiments, the Fc region of the antibody and/or fusion protein is modified at amino acid Leu235 (Boxed, Kabat Numbering) to alter Fc receptor interactions, e.g., Leu235Glu (L235E) or Leu235Ala (L235A). In some embodiments, the Fc region of the antibody and/or fusion protein is modified at amino acid Leu234 (Boxed, Kabat Numbering) to alter Fc receptor interactions, e.g., Leu234Ala (L234A). In some embodiments, the Fc region of the antibody and/or fusion protein is altered at both amino acid 234 and 235, e.g., Leu234Ala and Leu235Ala (L234A/L235A) or Leu234Val and Leu235Ala (L234V/L235A). In some embodiments, the Fc region of the antibody and/or fusion protein is lacking an amino acid at one or more of the following positions to reduce Fc receptor binding: Glu233 (E233, Bold in SEQ ID NO: 1), Leu234 (L234), or Leu235 (L235). In some embodiments, the Fc region of the antibody and/or fusion protein is altered at Gly235 to reduce Fc receptor binding. For example, wherein Gly235 is deleted from the antibody and/or fusion protein. In some embodiments, the human IgG1 Fc region is modified at amino acid Gly236 to enhance the interaction with CD32A, e.g., Gly236Ala (G236A, Boxed in SEQ ID NO: 1). In some embodiments, the human IgG1 Fc region is lacks Lys447, which corresponds to residue 218 of SEQ ID NO: 1 (EU index of Kabat et at 1991 *Sequences of Proteins of Immunological Interest*).

In some embodiments, the Fc region of the OprI targeting antibody or antigen-binding fragment thereof or the OprI-targeting fusion polypeptide includes a human IgG2 region. In some embodiments, the human IgG2 Fc region is modified at amino acid Asn297 (Boxed, to prevent to glycosylation of the antibody, e.g., Asn297Ala (N297A) or Asn297Asp (N297D). In some embodiments, the human IgG2 Fc region lacks Lys447, which corresponds to residue 217 of SEQ ID NO: 2 (EU index of Kabat et at 1991 *Sequences of Proteins of Immunological Interest*).

In some embodiments, the Fc region of the OprI targeting antibody or antigen-binding fragment thereof or the OprI-targeting fusion polypeptide includes a human IgG3 region. In some embodiments, the human IgG3 Fc region is modified at amino acid Asn297 (Boxed, Kabat Numbering) to prevent to glycosylation of the antibody, e.g., Asn297Ala (N297A) or Asn297Asp (N297D). In some embodiments, the human IgG3 Fc region is modified at amino acid 435 to extend the half-life, e.g., Arg435His (R435H, boxed in SEQ ID NO: 3). In some embodiments, the human IgG3 Fc region is lacks Lys447, which corresponds to residue 218 of SEQ ID NO: 3 (EU index of Kabat et at 1991 *Sequences of Proteins of Immunological Interest*).

In some embodiments, the Fc region of the OprI targeting antibody or antigen-binding fragment thereof or the OprI-targeting fusion polypeptide includes a human IgG4 region. In other embodiments, the human IgG4 Fc region is modified at amino acid 235 to alter Fc receptor interactions, e.g., Leu235Glu (L235E). In some embodiments, the human IgG4 Fc region is modified at amino acid Asn297 (Kabat Numbering) to prevent to glycosylation of the antibody, e.g., Asn297Ala (N297A) or Asn297Asp (N297D). In some embodiments, the human IgG4 Fc region is lacks Lys447, which corresponds to residue 218 of SEQ ID NO: 4 (EU index of Kabat et at 1991 *Sequences of Proteins of Immunological Interest*).

In some embodiments, the human IgG Fc region of the OprI targeting antibody or antigen-binding fragment thereof or the OprI-targeting fusion polypeptide is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, *J. Biol Chem* Vol 281(33) 23514-23524), Met428Leu and Asn434Ser (M428L, N434S) (Zalevsky et at 2010 *Nature Biotech*, Vol 28(2) 157-159), Met252Ile, Thr256Asp, Met428Leu (M252I, T256D, M428L, respectively) or Met252Tyr, Met428Leu/Val (M252Y, M428L/V, respectively), (EU index of Kabat et at 1991 *Sequences of Proteins of Immunological Interest*). Met252 corresponds to residue 23 in SEQ ID NOs: 1, 3, and 4 and residue 22 in SEQ ID NO: 2. Ser254 corresponds to corresponds to residue 25 in SEQ ID NOs: 1, 3, and 4 and residue 24 in SEQ ID NO: 2. Thr256 corresponds to residue 27 in SEQ ID NOs: 1, 3, and 4 and residue 26 in SEQ ID NO: 2. Met428 corresponds to residue 199 in SEQ ID NOs: 1, 3, and 4 and residue 198 in SEQ ID NO: 2. Asn434 corresponds to residue 205 in SEQ ID NOs: 1, 3, and 4 and residue 204 in SEQ ID NO: 2.

In some embodiments, the Fc region of the OprI targeting antibody or antigen-binding fragment thereof or the OprI-targeting fusion polypeptide is mutated or modified. In these embodiments, the mutated or modified Fc polypeptide includes the following mutations: Met252Tyr and Met428Leu (M252Y, M428L) using the Kabat numbering system.

In some embodiments, the human IgG Fc region of the OprI targeting antibody or antigen-binding fragment thereof or the OprI-targeting fusion polypeptide is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11. Examples of mutations that enhance ADCC include modification at Ser239 and Ile332, for example Ser239Asp and Ile332Glu (S239D, I332E). Examples of mutations that enhance CDC include modifications at Lys326 which corresponds to residue 97 of SEQ ID NOs: 1, 3, and 4 and residue 96 of SEQ ID NO: 2, and Glu333, which corresponds to residue 104 of SEQ ID NOs: 1, 3, and 4 and residue 103 of SEQ ID NO: 2. In some embodiments, the Fc region is modified at one or both of these positions, for example Lys326Ala and/or Glu333Ala (K326A and E333A) using the Kabat numbering system.

In some embodiments, the human IgG Fc region of the OprI targeting antibody or antigen-binding fragment thereof or the OprI-targeting fusion polypeptide is modified to induce heterodimerization. For example, having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, which corresponds to residue 137 of SEQ ID NOs: 1, 3, and 4 and residue 136 of SEQ ID NO: 2, Leu368, which corresponds to residue 139 of SEQ ID NOs: 1, 3, and 4 and residue 138 of SEQ ID NO: 2, and Tyr407, which corresponds to residue 178 of SEQ ID NOs: 1, 3, and 4 and residue 177 of SEQ ID NO: 2, e.g., Ser, Ala and Val, respectively (T366S/L368A/Y407V). Heterodimerization via CH3 modifications can be further stabilized by the introduction of a disulfide bond, for example by changing Ser354, which corresponds to residue 125 of SEQ ID NOs: 1, 3, and 4 and residue 124 of SEQ ID NO: 2, to Cys (S354C) and Y349, which corresponds to residue 120 of SEQ ID NOs: 1, 3, and 4 and residue 119 of SEQ ID NO: 2, to Cys (Y349C) on opposite CH3 domains (Reviewed in Carter, 2001 Journal of Immunological Methods, 248: 7-15). In some of these embodiments, the Fc region may be modified at the protein-A binding site on one member of the heterodimer so as to prevent protein-A binding and thereby enable more efficient purification of the heterodimeric fusion protein. An exemplary modification within this binding site is Ile253, which corresponds to residue 24 of SEQ ID NOs: 1, 3, and 4 and residue 23 of SEQ ID NO: 2, for example Ile253Arg (I253R). For example the I253R modification maybe combined with either the T366S/L368A/Y407V modifications or with the T366W modifications. The T366S/L368A/Y407V modified Fc is capable of forming homodimers as there is no steric occlusion of the dimerization interface as there is in the case of the T336W modified Fc. Therefore, in preferred embodiments the I253R modification is combined with the T366S/L368A/Y407V modified Fc to disallow purification any homodimeric Fc that may have formed.

In some embodiments, the human IgG Fc region of the OprI targeting antibody or antigen-binding fragment thereof or the OprI-targeting fusion polypeptide is modified to prevent dimerization. In these embodiments, the antibodies and/or fusion proteins of the present invention are monomeric. For example modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the fusion proteins of the present invention are operably linked via amino acid linkers. In some embodiments, these linkers are composed predominately of the amino acids Glycine and Serine, denoted as GS-linkers herein. The GS-linkers of the fusion proteins of the present invention can be of various lengths, for example 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., $(GGS)_2$ (SEQ ID NO: 75); GGSGGSGGS, i.e., $(GGS)_3$ (SEQ ID NO: 76); GGSGGSGGSGGS, i.e., $(GGS)_4$ (SEQ ID NO: 77); GGSGGSGGSGGSGGS, i.e., $(GGS)_5$ (SEQ ID NO: 45), GGGGS (SEQ ID NO: 78); GGGGSGGGGS, i.e., $(GGGGS_2)$ (SEQ ID NO: 79), and GGGGSGGGGSGGGGS, i.e., $(GGGGS_3)$ (SEQ ID NO: 80).

In some embodiments, the fusion protein is tetravalent. In some embodiments, the tetravalent fusion protein has the following structure: VHH-Linker-VHH-Linker-Hinge-Fc, where the VHH is a humanized or fully human VHH sequence. In some embodiments, the tetravalent fusion protein has the following structure: VHH-Linker-Hinge-Fc-Linker-VHH, where the VHH is a humanized or fully human VHH sequence.

In some embodiments, the fusion protein is hexavalent. In some embodiments, the hexavalent fusion protein has the following structure: VHH-Linker-VHH-Linker-VHH-Linker-Hinge-Fc, where the VHH is a humanized or fully human VHH sequence. In some embodiments, the hexavalent fusion protein has the following structure: VHH-Linker-VHH-Linker-Hinge-Fc-Linker-VHH, or VHH-Linker-Hinge-Fc-Linker-VHH-Linker-VHH where the VHH is a humanized or fully human VHH sequence.

In some embodiments, the fusion protein lacks an Fc region. In these embodiments, wherein the fusion protein is tetravalent, the protein has the following structure VHH-Linker-VHH-Linker-VHH-Linker-VHH-Linker. In these embodiments, wherein the fusion protein is pentavalent, the protein has the following structure VHH-Linker-VHH-Linker-VHH-Linker-VHH-Linker-VHH. In these embodiments, wherein the fusion protein is hexavalent, the protein has the following structure VHH-Linker-VHH-Linker-VHH-Linker-VHH-Linker-VHH-Linker-VHH. In these embodiments, the VHH is a humanized or fully human VHH sequence.

It will be appreciated that administration of therapeutic entities in accordance with the invention will be administered with suitable carriers, buffers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

BRIEF DESCRIPTION OF FIGURES

FIGS. 3A and 3B are a series of graphs depicting cytotoxicity analysis using various VPBP-containing fusion proteins of the disclosure. The A549 cell line was used as the target cell line.

FIGS. 4A, 4B, and 4C are a series of graphs depicting survival analysis in an infection model using various VPBP-containing fusion proteins of the disclosure. The V2L2 mAb was used a positive control as PCRV blocking antibody.

FIG. 5 is a graph depicting binding of an example OprI antibody to bind to a variety of *Pseudomonas aeruginosa* strains and to *Pseudomonas putida*.

FIG. 7 is a graph depicting the ability of various VPBP-containing fusion proteins of the disclosure to provide superior protection in vivo in *P. aeruginosa* prophylaxis-pneumonia model. Included herein is an exemplary multi-specific, PCRV-OprI (PCRV-18-15-OprI-7), fusion protein of the disclosure demonstrating enhanced protective capacity over a bispecific targeting PCRV and PSL (disclosed in US20150284450 and DiGiandomenico et al., "A multifunctional bispecific antibody protects against Pseudomonas aeruginosa," Sci Transl Med., vol. 6(262): 262ra155 (2014)) at equivalent molar dose.

DETAILED DESCRIPTION

Figure 1:
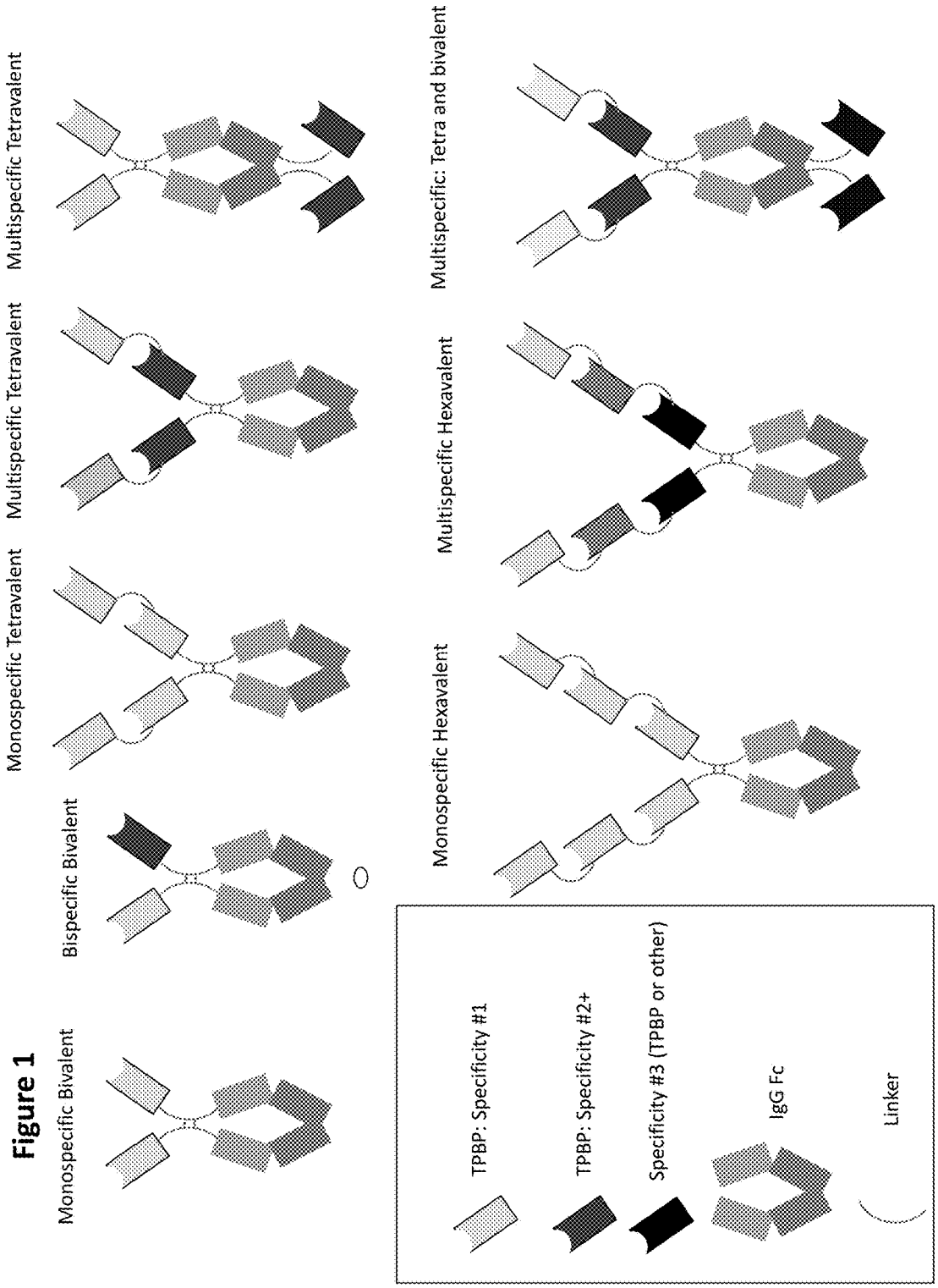
FIG. 1 is a series of schematic representations of exemplary VPBP-containing fusion proteins of the present disclosure. VPBP recognizing distinct epitopes are differentially shaded in these schematic representations.
Figure 2A:
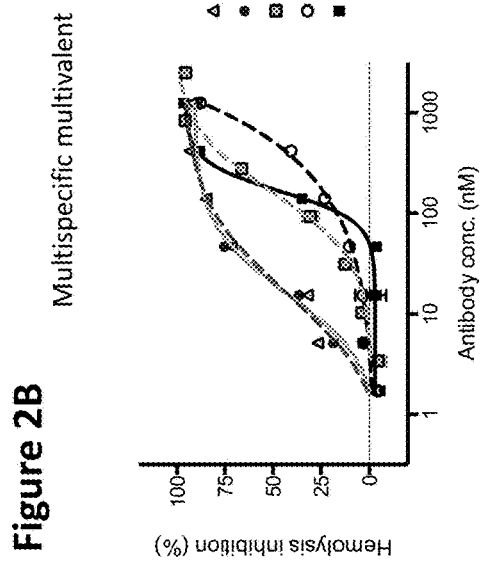
FIGS. 2A, 2B, and 2C are a series of graphs depicting hemolysis analysis using various VPBP-containing fusion proteins of the disclosure.
Figure 2B:
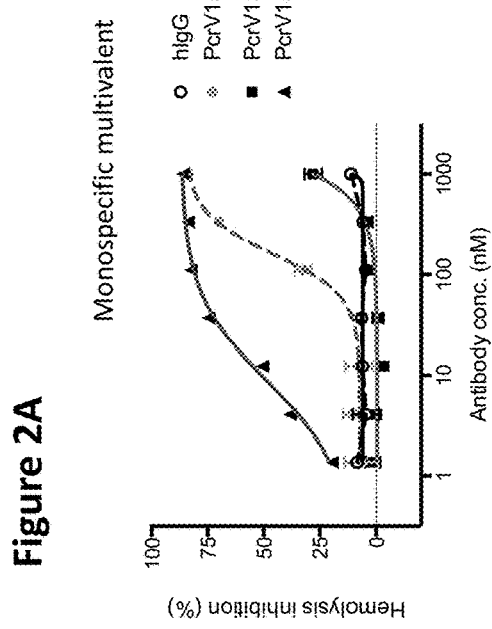
Figure 2C:
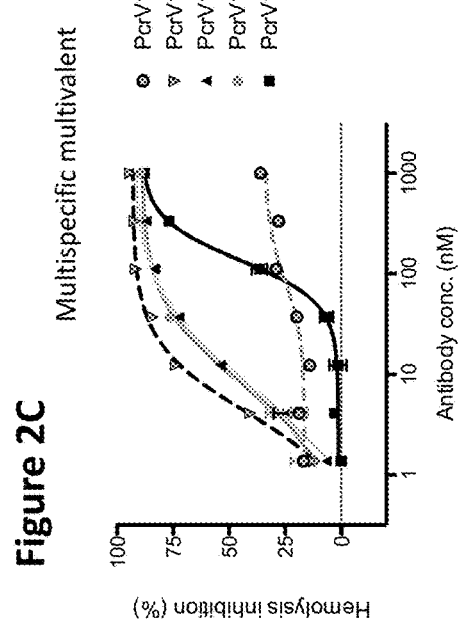

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. The term patient includes human and veterinary subjects.

As utilized in accordance with the present disclosure, the following terms, unless otherwise indicated, shall be understood to have the following meanings:

As used herein, the terms "targeting fusion protein" and "antibody" can be synonyms. As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, Fab, Fab' and F(ab')$_2$ fragments, F$_v$, scFvs, an Fab expression library, and single domain antibody (sdAb) fragments, for example $V_HH$, $V_{NAR}$, engineered $V_H$ or $V_K$.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses (also known as isotypes) as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

The single domain antibody (sdAb) fragments portions of the fusion proteins of the present invention are referred to interchangeably herein as targeting polypeptides herein.

As used herein, the term "epitope" includes any protein determinant capable of specific binding to/by an immunoglobulin or fragment thereof, or a T-cell receptor. The term "epitope" includes any protein determinant capable of specific binding to/by an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; e.g., ≤100 nM, preferably ≤10 nM and more preferably ≤1 nM.

As used herein, the terms "immunological binding" and "immunological binding properties" and "specific binding" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($k_{on}$) and the "off rate constant" ($k_{off}$) can be determined by calculation of the concentrations and the actual rates of association and dissociation. (See Nature 361:186-87 (1993)). The ratio of $k_{off}/k_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to an antigen, when the equilibrium binding constant ($K_d$) is ≤1 µM, preferably ≤100 nM, more preferably ≤10 nM, and most preferably ≤100 pM to about 1 pM, as measured by assays such as radioligand binding assays, surface plasmon resonance (SPR), flow cytometry binding assay, or similar assays known to those skilled in the art.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to CD47, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH-(cis and trans), —$COCH_2$—, $CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, and/or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$ $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

As used herein, the terms "treat," treating," "treatment," and the like refer to reducing and/or ameliorating a disorder and/or symptoms associated therewith. By "alleviate" and/or "alleviating" is meant decrease, suppress, attenuate, diminish, arrest, and/or stabilize the development or progression of a disease such as, for example, a cancer. It will be appreciated that, although not precluded, treating a disorder or condition does not require that the disorder, condition or symptoms associated therewith be completely eliminated.

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

By "effective amount" is meant the amount required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "subject" is meant a mammal, including, but not limited to, a human or non-human mammal, such as a bovine, equine, canine, rodent, ovine, primate, camelid, or feline.

The term "administering," as used herein, refers to any mode of transferring, delivering, introducing, or transporting a therapeutic agent to a subject in need of treatment with such an agent. Such modes include, but are not limited to, oral, topical, intravenous, intraperitoneal, intramuscular, intradermal, intranasal, and subcutaneous administration.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Therapeutic formulations of the invention, which include a V-tip protein targeting molecule of the invention, are used to treat or alleviate a symptom associated with a disease or disorder associated with aberrant activity and/or expression of one or more V-tip proteins of Gram negative bacteria, such as PcrV from *Pseudomonas aeruginosa*, in a subject. A therapeutic regimen is carried out by identifying a subject, e.g., a human patient suffering from (or at risk of developing) a disease or disorder associated with aberrant activity and/or expression of one or more V-tip proteins of Gram negative bacteria, such as PcrV from *Pseudomonas aeruginosa*, using standard methods, including any of a variety of clinical and/or laboratory procedures. The term patient includes human and veterinary subjects. The term subject includes humans and other mammals.

Efficaciousness of treatment is determined in association with any known method for diagnosing or treating the particular disease or disorder associated with aberrant activity and/or expression of one or more V-tip proteins of Gram negative bacteria, such as PcrV from *Pseudomonas aeruginosa*. Alleviation of one or more symptoms of the disease or disorder associated with aberrant activity and/or expression of one or more V-tip proteins of Gram negative bacteria, such as PcrV from *Pseudomonas aeruginosa*, indicates that the V-tip protein targeting molecule confers a clinical benefit.

Methods for the screening of V-tip protein targeting molecules that possess the desired specificity include, but are not limited to, enzyme linked immunosorbent assay (ELISA), enzymatic assays, flow cytometry, and other immunologically mediated techniques known within the art.

The invention will be further described in the following examples, which do not limit the scope of the invention described in the claims.

Example 1: Hemolysis Blocking

The ability of the VPBPs of the present invention to block bacterial induced hemolysis of red blood cells (RBCs) can be assessed by numerous protocols known in the art. For example, human RBCs were washed in PBS and resuspended at 2% (v/v) in DMEM. *Pseudomonas aeruginosa* bacteria plus serially diluted antibodies were added to RBCs in 96 well round bottom plates. The plates were incubated for 2 h at 37° C. and then 2 h at 4° C. The plates were then spun to pellet intact RBCs, after which the supernatant was transferred to a flat bottom 96-well plate for spectrophotometric observation of released hemoglobin.

As shown in FIGS. 2A-2D, both monospecific and multispecific multivalent VPBPs of the present invention are able to block bacterial induced hemolysis of RBCs.

Example 2: Cytotoxicity Blocking

The ability of the VPBPs of the present invention to block bacterial induced cytotoxicity of mammalian cells can be assessed by numerous protocols known in the art. For example, A confluent monolayer of A549 (lung epithelial) cells were grown in 96-well plates. Cells were loaded with Calcein AM and then washed to remove excess Calcein. *P. aeruginosa* and antibodies at varying concentrations were added to the A549 cells and incubated for 2 h at 37° C. Monolayers were then washed, after which the remaining cells were quantified by fluorescence.

As shown in FIGS. 3A-3B, both monospecific and multispecific multivalent VPBPs of the present invention are able to block bacterial induced cytotoxicity of mammalian cells.

Example 3: *Pseudomonas aeruginosa* Infection Model

The ability of the VPBPs of the present invention to protect against a bacterial infection can be assessed using a mouse model of *P. aeruginosa* infection. Mice were pretreated with PcrV antibodies 24 h prior to infection with *P. aeruginosa*. At t=0 mice were intratracheally infected with *P. aeruginosa* and survival was monitored for 4 days. Importantly, it was discovered that the multispecific multivalent VPBP-containing fusion proteins conferred substantially more protection compared to monospecific multivalent VPBP-containing fusion proteins (FIGS. 4A-4C). The multispecific multivalent VPBP-containing fusions of the present invention also are substantially more potent than the anti-PCRV antibody, V2L2, known in the art to be a potent blocker of *P. aeruginosa* induced hemolysis (see e.g., PCT/US2012/063639, published as WO 2013/0170565).

Example 4: OprI Antibodies Bind to Multiple Strains

The ability of OprI targeting antibodies to bind to *Pseudomonas* strains can be assessed by whole cell bacterial ELISA. Bacterial cultures were grown to mid-logarithmic phase in standard bacteriologic media, then washed and resuspended in PBS. Equal volumes of bacterial suspension were placed in 96 well plates and incubated at 37 C for 24 h. Plates were blocked with BSA and then serial dilutions of antibodies were added. After subsequent washing, HRP-conjugated anti-human Fc specific secondary antibody was added. Following incubation and washing, TMB substrate was added and absorbance at 600 nm was measured to detect binding of antibodies to bacteria. As shown in FIG. 5, OprI antibodies were found to bind to all strains of *Pseudomonas aeruginosa* tested, as well as *Pseudomonas putida*.

Example 5: Bispecific Molecules in *Pseudomonas aeruginosa* Infection Model

The studies presented herein demonstrate the ability of the VPBPs of the present invention to protect against a bacterial infection can be assessed using a mouse model of *P. aeruginosa* infection. In particular, these studies use a VPBP that binds both PcrV and outer membrane protein I ("OprI"), also referred to herein as "PcrV×OprI bispecific fusion proteins," "PcrV×OprI fusion proteins" and/or "PcrV×OprI fusions." Dual targeting of PcrV and OprI allows the fusion polypeptides to tether or otherwise attach and/or bind to the bacteria cell surface, and the studies provided herein demonstrate that this dual-targeting also produces enhanced protection in vivo.

Figure 6:
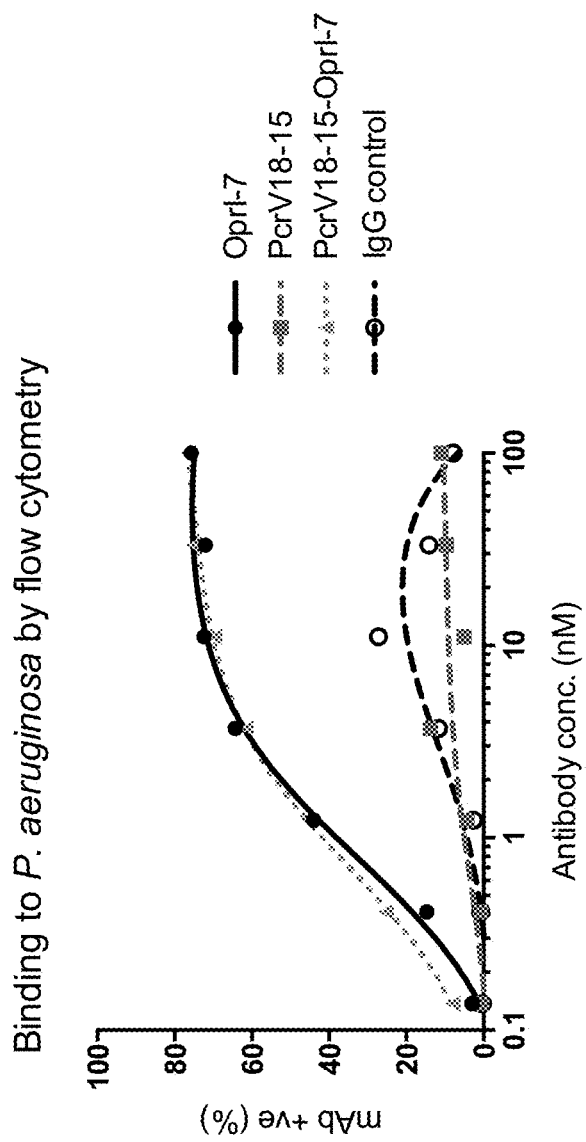
FIG. 6 is a graph depicting the ability of various VPBP-containing fusion proteins of the disclosure to bind *P. aeruginosa* via OprI.

The PcrV×OprI bispecific fusions target the bacterial cell surface by targeting OprI. FIG. 6 demonstrates that the PcrV×OprI bispecific fusions of the disclosure bind to *P. aeruginosa* by flow cytometry.

The PcrV×OprI bispecific fusions also are more potent in vivo than the bispecific molecule Bis4, which binds PcrV and PSL and is known in the art to be a blocker *P. aeruginosa* induced hemolysis (see e.g., DiGiandomenico et al., "*A multifunctional bispecific antibody protects against Pseudomonas aeruginosa,*" Sci Transl Med., vol. 6(262): 262ra155 (2014)). FIG. 7 demonstrates that the PcrV×OprI bispecific fusion proteins provide superior protection in vivo in a *P. aeruginosa* pneumonia-prophylaxis animal model.

TABLE 1

PcrV-VPBP Sequences

PcrV1A (1A7)
EVQLVQSGGGLVQAGGSLRLSCAASGRIFGTYGMGWFRQAPGKERVFVAAISKSGPTT
YYADSVKGRFTISRDNAENTVYLQMNSLKPEDTAVYYCGASSHSMLVVTTSQVDYW
GRGTQVTVSS (SEQ ID NO: 10)

PcrV2A (1B9)
EVQLVQSGGGLVQPGGSLRLSCAVSGLIFDNYGIGWFRQAPEKEREGVSCIHESDGSTY
YTDSVKGRFAISRDNAKNTGYLEMNNLKPEDTAVYYCVVLSYVSRCPEGSKYDYWG
QGTQVTVSS (SEQ ID NO: 11)

PcrV3A (1B12)
EVQLVQSGGGLVQPGGSLRLSCAASGFTLDYYP1GWFRQAPGKEREGVSC1SSSEGSTY
YADSVXGRFTISRDNAKNTVYLQMNNMKPEDTAVYYCATDFFTTGCPSGGGKYDYVV
GQGTQVTVSS (SEQ ID NO: 12)

PcrV4A (1G9)
EVQLVQSGGGLVRAGGSLRLSCAPSERTFGSFGMGWFRQAPGKEREFVAALMWGTSY
TSYADSVKGRFTVSKDNAKNTLYLQMNSLKPEDTAVYYCAAGAVGADPRRYDYWG
QGTQVTVSS (SEQ ID NO: 13)

PcrV5A (2A5)
EVQLVQSGGGLVQAGGSLRLSCAASGLAFRNYRMGWFRQAPGKEREFVAAISGNIGG
SGVGTDYADSVKGRFTISRDNDKDTAYLQMNSLKPEDTAVYYCAADHHLTMLPGEY
DFWGEGTQVTVSS (SEQ ID NO: 14)

PcrV6A (2A11)
EVQLVQSGGGLVQPGGSLRLSCAASGSTLDYYAIGWFRQAPGKEREGVACISSSDGST
DYADSMKGRFTISRDNAOKTVYLO-MNSLKPEDTAVYSCAAVAFFCGSSWYLSSGMD
YWGKGTQ VTVSS (SEQ ID NO: 15)

PcrV7A (2A12)
EVQLVQSGGGLVQAGGSLRLSCAASGGTFSSNAMYWYRQAPGKQRELVASISGTSNA
NYPDSVKGRFTISRDNAKNTVTLQMNSLKPEDTAVYYCRAAPVSGPLIGRIFWGQGTQ
VTVSS (SEQ ID NO: 16)

PcrV8A (2B4)
EVQLVQSGGGLVQAGGSLRLSCATSGLTFSVYAMGWFRQAPGKQREFVARITAGGSG
TYYADSMEGRFTISRDNARNTVYLQMNSLKPEDTAVYYCAAARIIWTRGTEHLPTAY
DYWGQGTQVTVSS (SEQ ID NO: 17)

PcrV9A (2B7)
EVQLVQSGGGLVQAGGSLRLSCASSGSTFRTYGMGWFRQPPGKQRHWVAGMAIDGL
TTYADSAKGRFTASRDNARNIVYLQMNELKPEDTAVYYCYAAGYWGQGTQVTVSS
(SEQ ID NO: 18)

PcrV10A (2G6)
EVQLVQSGGGLVQAGGSLRLSCTTSGITFSDNAMYWYRQAPGKQRELVASISSGGWT
NYADSVKGRFT1SRDNVKNTVTLQMNSLEPEDTALYYCRAAPVRGNFIGRVFWGQGT
QVTVSS (SEQ ID NO: 19)

TABLE 1 -continued

PcrV-VPBP Sequences

PcrV11A (4H7)
EVQLVQSGGGLVQPGGSLRLSCAAFGSIFTIGTMGWYRQAPGKQRELVATITRGSSTN
YADSVKGRFTISID SAKNTVYLQMNSLKSEDTAVYYCAADRGAVGPAMRVVADYWG
QGTQVTVSS (SEQ ID NO: 20)

PcrV12A (3B7)
EVQLVQSGGGLVQAGGSLRLSCAASGSTFSSNAMYWYRQAPGKQRELVASISDGGFT
TYYADSVKGRFTISKDNAENTVYLOMNIMKPEDTAVYYCAASISSRVVVHTAOADYW
GQGTQVTVSS (SEQ ID NO: 21)

PcrVI3A (4G2)
EVQLVQSGGGLVQPGGSLRLPCAASGSIFTIGTMGWYRQAPGKQRELVATITRGSSTN
YADSVKDRFTISRDNAKRTLHLQMNGLKAEDTAVYYCATDLFENSCPLKHDFWGQGT
QVTVSS (SEQ ID NO: 22)

PcrV14A (4G10)
EVQLVQSGGGLVQAGGSLRLSCAASGSTFSSNAMYWYRQAPGKQRELVASISDGGFT
YADSVKGRFTISRDNGRNTAYLQMNSLQEEDTAVYYCHADPVFTPGRNDYWGQGTQ
VTVSS (SEQ ID NO: 23)

PcrV15A (4G9)
EVQLVQSGGGLVQPGESLRLSCAASGSIFSINTMVWYRQVPGKQRELVASITNQGIPHY
ADSVKGRFTISRENAKNTVNLQMNSLKPEDTAVYVCNAWIRSDGVSPYLNYWGQGT
QVTVSS (SEQ ID NO: 24)

PcrV16A (3B10)
EVQLVQSGGGLVQPGGSLGLSCVGSGSISGIHTMGWYRRAPGNQRELIATATSAGITN
YSESVKGRKTISRDNAKSTVYLQMSSLKPEDTGVYYCNDVFGRTSWGQGTQVTVSS
(SEQ ID NO: 25)

PcrV17A (3G1)
EVQLVQSGGGLVQPGGSLRLSCAASGNIFGGNVMGWYRQAPGKQRELVAGIGSLGRT
TYADSVKGRFSISRDNAKNTVYLQMDSLKPEDTAVYYCNVVRLGGPDYWGQGTQVT
VSS (SEQ ID NO: 26)

PcrV18A (3F2)
EVQLVQSGGGLVQAGGSLRLSCTTSGNTFSDNAMYWYRQAPGKQREVASISSGGWT
NYADSVKGRFTISRDNVKNTVTLQMDRLEPEDTALYYCRAAPVRGYLIGRVFWGQGT
QVTVSS (SEQ ID NO: 27)

PcrV19A (4E12)
EVQLVQSGGGLVQAGGSLRLSCSASGSNSIFNMGWYRQRPGRQRELVALISSGTGSTS
YAGSVKGRFAISRDNAKATVYLQMNSLKLEDTAVYYCRITTDNARLVYWGQGTQVT
VSS (SEQ ID NO: 28)

PcrV20A (3C1)
EVQLVQSGGGLVQPGGSLRLSCSCAASGRIFSVNNMGWYRQTPGKQRELVAVITVNGITT
YSDSVKGRFTLSRDNAKNTIYLQMNSLKPEDTAVYSCYGYIRLAATNPYVQYWGQGT
QVTVSS (SEQ ID NO: 29)

PcrV21A (3C7)
EVQLVQSGGGLVQPGGSLRLSCAASGSIFSINTMGWYRQAPGNQRDIVATITMNGVPH
YADAVKGRFTISRDNAKNTVYLQMNGLKPEDTAVYYCNAWINLYGSPPLQNYWGQG
TQVTVSS (SEQ ID NO: 30)

PcrV22A (4H8)
EVQLVQSGGGLVQAGGSLRLSCAASGSIFSINAMGWYRQAPGKQRELVTSITNQGIPH
YADSVKGRFTISRKNAKNTVNLQMNSLKPEDTAVYVCNAW1RGDGGSPYI.NYWGQG
TQVTVSS (SEQ ID NO: 31)

PcrV23A (1G6)
EVQLVQSGGGLVQPGESLRLSCAASGSIFSINTMVWYRQVPGKQRELVASITNQGIPHY
ADSVKGRFTISRENAKNTVNLQMNSLKPEDTAVYVCNAWIRSDGVPPYLNYWGQGT
QVTVSS (SEQ ID NO: 32)

PcrV24A (2E1)
EVQLVQSGGGLVQPGGSLRLSCAASGSIFNINSMHWYRQAPGNQRELVASISKGGITN
YADSVKGRFAISRDDAQNTLYLQMNSLKPEDTAVYYCNAWISEIATGPILYNYWGQG
TQVTVSS (SEQ ID NO: 33)

PcrV25A (1F9)
EVQLVQSGGGLVQPGGSLSLSCAASGSVFSINRMAWYRQAPGKQRELVADIGTMGAS
DYADSVKGRI IISRDNAKK IVDI.QMNSLKPEDTAVYFCNAWMRGAPDVAYTNYWG
QGTQVTVSS (SEQ ID NO: 34)

TABLE 1 -continued

PcrV-VPBP Sequences

PcrV26A (4H1)
EVQLVQSGGGLVQPGGSLRLSCAASGRVVSINNMGWYQQTPGNQRKLVAIITLNGVTT
YADSVKGRFTISRDNAKNTVYLQMASLKPEDTAIYYCNAWVRTVPGSAYSNYWGQG
TQVTVSS (SEQ ID NO: 35)

PcrV27A (1B4)
EVQLVQSGGDLVQPGGSLRLSCAASGRIFSVNNMGWYRQAPGKQRELVAVITMNGVT
TYEDSVKGRFTLSRDNAKNTIYLQMNSLKPEDTAVYFCYGYIRLAATNPYVQYWGQG
TQVTVSS (SEQ ID NO: 36)

hzPcrV15v1
EVQLLESGGGEVQPGGSLRLSCAASGSIFSINTMVWYRQAPGKQRELVSSITNQGIPHY
AESVKGRFTISRDNAKNTLYLQMSSLRAEDTAVYYCNAWIRSDGVSPYLNYWGQGTL
VTVKP (SEQ ID NO: 37)

hzPcrV15v2
EVQLLESGGGEVQPGGSLRLSCAASGSIFSINTMVWYRQAPGKQRELVSSITNQGIPHY
AESVKGRFTISRDNAKNTLYLQMSSLRAEDTAVYYCNAWIRSYGVSPYLNYWGQGTL
VTVKP (SEQ ID NO: 38)

hzPcrV15v3
EVQLLESGGGEVQPGGSLRLSCAASGSIFSINTMVWYRQAPGKQRELVSSITNQGIPHY
AESVKGRFTISRDNAKNTLYLQMSSLRAEDTAVYYCNAWIRSEGVSPYLNYWGQGTL
VTVKP (SEQ ID NO: 39)

hzPcrV15v4
EVQLLESGGGEVQPGGSLRLSCAASGSIFSINTMVWYRQAPGKQRELVSSITNQGIPHY
AESVKGRFTISRDNAKNTLYLQMSSLRAEDTAVYYCNAWIRSQGVSPYLNYWGQGTL
VTVKP (SEQ ID NO: 40)

hzPcrV15DAv5
EVQLLESGGGEVQPGGSLRLSCAASGSIFSINTMVWYRQAPGKQRELVSSITNQGIPHY
AESVKGRFTISRDNAKNTLYLQMSSLRAEDTAVYYCNAWIRSDAVSPYLNYWGQGTL
VTVKP (SEQ ID NO: 41)

hzPcrV15DTv6
EVQLLESGGGEVQPGGSLRLSCAASGSIFSINTMVWYRQAPGKQRELVSSITNQGIPHY
AESVKGRFTISRDNAKNTLYLQMSSLRAEDTAVYYCNAWIRSDTVSPYLNYWGQGTL
VTVKP (SEQ ID NO: 42)

hzPcrV15v7
EVQLLESGGGEVQPGGSLRLSCAASGSIFSINTMVWYRQAPGKGRELVSSITNQGIPHY
AESVKGRFTISRDNAKNTLYLQMSSLRAEDTAVYYCNAWIRSQGVSPYLNYWGQGTL
VTVKP (SEQ ID NO: 81)

hzPcrV15v8
EVQLLESGGGEVQPGGSLRLSCAASGSIFSINTMVWYRQAPGKGLELVSSITNQGIPHY
AESVKGRFTISRDNAKNTLYLQMSSLRAEDTAVYYCNAWIRSQGVSPYLNYWGQGTL
VTVKP (SEQ ID NO: 82)

hzPcrV18
EVQLLESGGGEVQPGGSLRLSCAASGNTFSDNAMYWYRQAPGKQRELVSSISSGGWT
NYAESVKGRFTISRDNAKNTLYLQMSSLRAEDTAVYYCRAAPVRGYLIGRVFWGQGT
LVTVKP (SEQ ID NO: 43)

hzPcrV18v2
EVQLLESGGGEVQPGGSLRLSCAASGNTFSDNAMYWYRQAPGKGRELVSSISSGGWT
NYAESVKGRFTISRDNAKNTLYLQMSSLRAEDTAVYYCRAAPVRGYLIGRVFWGQGT
LVTVKP (SEQ ID NO: 83)

hzPcrV18v3
EVQLLESGGGEVQPGGSLRLSCAASGNTFSDNAMYWYRQAPGKGLELVSSISSGGWT
NYAESVKGRFTISRDNAKNTLYLQMSSLRAEDTAVYYCRAAPVRGYLIGRVFWGQGT
LVTVKP (SEQ ID NO: 84)

hzPcrV20v1
EVQLLESGGGEVQPGGSLRLSCAASGRIFSVNNMGWYRQAPGKQRELVSVITVNGITT
YAESVKGRFTISRDNAKNTLYLQMSSLRAEDTAVYYCYGYIRLAATNPVQYWGQGT
LVTVKP (SEQ ID NO: 44)

hzPcrV20v2
EVQLLESGGGEVQPGGSLRLSCAASGRIFSVNNMGWYRQAPGKQRELVSVITVGGITT
YAESVKGRFTISRDNAKNTLYLQMSSLRAEDTAVYYCYGYIRLAATNPVQYWGQGT
LVTVKP (SEQ ID NO: 71)

TABLE 1-continued

PcrV-VPBP Sequences hzPcrV20v3
EVQLLESGGGEVQPGGSLRLSCAASGRIFSVNNMGWYRQAPGKQRELVSVITVQGITT
YAESVKGRFTISRDNAKNTLYLQMSSLRAEDTAVYYCYGYIRLAATNPYVQYWGQGT
LVTVKP (SEQ ID NO: 72)

hzPcrV20v4
EVQLLESGGGEVQPGGSLRLSCAASGRIFSVNNMGWYRQAPGKQRELVSVITNQGITT
YAESVKGRFTISRDNAKNTLYLQMSSLRAEDTAVYYCYGYIRLAATNPYVQYWGQGT
LVTVKP (SEQ ID NO: 73)

hzPcrV20v5
EVQLLESGGGEVQPGGSLRLSCAASGRIFSVNNMGWYRQAPGKQRELVSVITVSGITT
YAESVKGRFTISRDNAKNTLYLQMSSLRAEDTAVYYCYGYIRLAATNPYVQYWGQGT
LVTVKP (SEQ ID NO: 74)

hzPcrV20v6
EVQLLESGGGEVQPGGSLRLSCAASGRIFSVNNMGWYRQAPGKQRELVSVITNQGITT
YAESVKGRFTISRDNAKNTLYLQMSSLRAEDTAVYYCYGYIRLAATNPYVQYWGQGT
LVTVKP (SEQ ID NO: 85)

hzPcrV20v7
EVQLLESGGGEVQPGGSLRLSCAASGRIFSVNNMGWYRQAPGKGLELVSVITNQGITT
YAESVKGRFTISRDNAKNTLYLQMSSLRAEDTAVYYCYGYIRLAATNPYVQYWGQGT
LVTVKP (SEQ ID NO: 86)

hzPcrV20v8
EVQLLESGGGEVQPGGSLRLSCAASGRIFSVNNMGWYRQAPGKGLEWVSVITNQGITT
YAESVKGRFTISRDNAKNTLYLQMSSLRAEDTAVYYCYGYIRLAATNPYVQYWGQGT
LVTVKP (SEQ ID NO: 87)

TABLE 2

OprI Binding Protein Sequences

OprI-VHH-1 (also referred to herein as "OprI-1")
QLQLQESGGGLVQSGRSLRLSCSASGSLFRFDTVWWYRQAPGKQREWVAYITAGGMT
NYADSVKGRFTISKDNAKNMVYLQMDSLLPEDTAVYYCNVGRNWGQGTQVTVSS
(SEQ ID NO: 46)

OprI-VHH-2 (also referred to herein as "OprI-2")
EVQLVQSGGGLVQPGESLRLSCAASGNIFRFDTVWWYRQPPGEQREWVSYITAGSITN
YADSVKGRFTISRDNAKNMVYLQMDNLKPEDTAVYYCRVGGSSWGQGTQVTVSS
(SEQ ID NO: 47)

OprI-VHH-3 (also referred to herein as "OprI-3")
EVQLVQSGGGLVQAGDSLRLSCAASGGISSTYAMGWFRQAPGKEREFVASIRLGSEAT
YYADSVKGRFTISRDNALKTIYLQMNSLKPDDTAVYYCAVDASLFLVTVDYWGRGTQ
VTVSS (SEQ ID NO: 48)

OprI-VHH-4 (also referred to herein as "OprI-4")
QVQLVQSGGGLVQAGGSLRLSCAASGRTFSRCVMGWFRQAPGKEREFVATISWSGAS
TVYADSVKGRFTISRENAKNTVYLQMNSLKPEDTAVYYCAAAESSWNGDIRLKGYDY
WGQGTQVTVSS (SEQ ID NO: 49)

OprI-VHH-5 (also referred to herein as "OprI-5")
QVTLKESGGGLVQAGGSLRLSCAASGRSFRTYTMAWFRQPPGKEREFVAAITWSGGS
TFYADPVKGRFTISRDNAKNTVYLQMNTLKPEDTAVYYCAVETSISGRYTVFQPRFYD
SWGQGTQVTVSS (SEQ ID NO: 50)

OprI-VHH-6 (also referred to herein as "OprI-6")
QVQLQESGGGLVQPGESLRLSCAASGNIFRFDTVWWYRQPPGEQREWVSYITAGSITN
YADSVKGRFIISRDNAKNMVYLQMDNLKPEDTAVYYCRVGGSSWGQGTQVTVSS
(SEQ ID NO: 51)

OprI-VHH-7 (also referred to herein as "OprI-7")
EVQLVQSGGGLVQPGGSLRLSCIASGSIFSTKTMGWYRQAPGKQREWVALITTGLSTQ
YLDSLEGRFTISRDNANNRVFLQMNNLKPEDTGVYYCNVVPGRGATYWGKGTQVTV
SS (SEQ ID NO: 52)

OprI-VHH-8 (also referred to herein as "OprI-8")
QLQLQESGGGLVQPGRSLRLSCAGSGSIFRYDTVWWYRQAPGKQREWVAYVTAGGIT
NYADSVKGRFTISKDNAKNMVYLQMDSLLPEDTAVYYCHVGRNWGQGTQVTVSS
(SEQ ID NO: 53)

TABLE 2-continued

OprI Binding Protein Sequences

OprI-VHH-9 (also referred to herein as "OprI-9")
QLQLQESGGGLVQAGGSLRLSCAASGRTFSSNVYSMGWFRQAPGKEREFVSAITWRG
GTTYYADSVKDRFTISKDNAKNTVYLQMNSLKSEDTAVYYCACSRMDSTRYDYWGQ
GTQVTVSS (SEQ ID NO: 54)

OprI-VHH-11 (also referred to herein as "OprI-11")
EVQLVQSGGGLVQSGRSLRLSCSASGSLFRFDTVWWYRQAPGKQREWVAYITAGGIT
NYADSVKGRFTISKDNAKNMVYLQMDSLLPEDTAVYYCSVGRNWGQGTQVTVSS
(SEQ ID NO: 55)

OprI-VHH-12 (also referred to herein as "OprI-12")
QVQLQESGGGLVQPGGSLRLSCAASGITVRINTMGWYRQAPGKQRELVAYITSGGITN
YVDSVKGRFTIARDDAKNTVYLQMNSLKPEDTAVYYCNVHGWRDFWGQGTQVTVSS
(SEQ ID NO: 56)

OprI-VHH-13 (also referred to herein as "OprI-13")
QVQLVQSGGGLVQPGGSLRLSCAASGTIFRFNTMAWYRQAPGKQREFVAYITWAGMT
GYQDSVQDRFTISRDNAKNTVSLQMNNLKPEDTAVYFCNKHGSSFVRDYWGQGTQV
TVSS (SEQ ID NO: 57)

OprI-VHH-14 (also referred to herein as "OprI-14")
EVQLVQSGGGLVQPGGSLRLSCAAAGSDFAIGAMGWYRQAPGKQRDFVAHITSGGIPS
FADSVKGRFTLSRDNAKNTVYLQMDSLKPDDTAVYYCYLRKRGSTTTWGQGTQVT
VSS (SEQ ID NO: 58)

OprI-VHH-15 (also referred to herein as "OprI-15")
QVQLQESGGGLVQAGGSLRLSCAASGRIFSNCVMGWFRQAPGKEREFVAAISWSGDT
THYADSLKGRFAISRDNANNTVFLQKDSLTPSDTAVYYCAASSRITSCQAMGVVPLLQ
PWYDYWGRGTQVTVSS (SEQ ID NO: 59)

OprI-VHH-16 (also referred to herein as "OprI-16")
QVQLQESGGGLVQPGRSLRLSCAASGNIFRFDTVWWYRQAPGKQREWVAYVTAGGIT
NYADSVKGRFTISKDNAKNIVYLHTDNLAPEDTAVYYCRVGQNWGQGTQVTVSS
(SEQ ID NO: 60)

OprI-VHH-17 (also referred to herein as "OprI-17")
QLQLQESGGGLVQPGGSPRLSCAASESIFRFNTMAWYRQAPGKQRELVAYITWAGRT
DYGDFVKGRFTISRDNAKNTVSLQMNSLKPEDTAVYYCNKHGSRFERDYWGQGTQV
TVSS (SEQ ID NO: 61)

OprI-VHH-18 (also referred to herein as "OprI-18")
QVQLQESGGDLVQPGGSLRL SCVASETIFRFNTMAWYRQAPGKRRELVGYITWAGRT
GYGDFVEGRFTISRDNSKNTVSLQMNSLKPEDTAVYYCNKHGSSFTQDYWGQGTQVT
VSS (SEQ ID NO: 62)

OprI-VHH-19 (also referred to herein as "OprI-19")
QLQLQESGGDLVQPGGSLRLSCVASETIFRFNTMAWYRQAPGKRRELVGYITWAGRT
GYGDFVEGRFTVSRDNSKNTVSLQMNSLKPEDTAVYYCNKHGASFTQDYWGQGTQV
TVSS (SEQ ID NO: 63)

OprI-VHH-21 (also referred to herein as "OprI-21")
QLQLQESGGGLVRPGSSLTLSCVASETIFRFNTMAWYRQAPGKRRELVGYITWAGRTG
YGDFVEGRFTISRDNSKNTVSLQMNSLEPEDTADYYCNKHGSSFLRDYWGQGTQVTV
SS (SEQ ID NO: 64)

OprI-VHH-22 (also referred to herein as "OprI-22")
QVQLQESGGGLVQPGRSLRLSCAGSGSMFRFDTVWWYRQAPGKQRDWVSYITAGSIA
NYADSVKGRFTISRDNTKNMVYLQMDSLKPEDTAVYYCRVGGNSWGQGTQVTVSS
(SEQ ID NO: 65)

OprI-VHH-23 (also referred to herein as "OprI-23")
QVQLQQSGGGLVQPGGSLRLSCEASSNIFRFNTMAWYRQAPGKQREFAAYITWAGLT
GYGDSLKGRFIISRDNAKNIVTLQMNSLKPEDTAVYYCNKHGSDFVRDYWGQGTQVT
VSS (SEQ ID NO: 66)

hzOprI-7v1 (also referred to herein as "OprI-7v1")
EVQLLESGGGEVQPGGSLRLSCAASGSIFSTKTMGWYRQAPGKQREWVSLITTGLSTQ
YAESVKGRFTISRDNANNTVYLQMSSLRAEDTAVYYCNVVPGRGATYWGQGTLVTV
KP (SEQ ID NO: 67)

hzOprI-7v2 (also referred to herein as "OprI-7v2")
EVQLLESGGGEVQPGGSLRLSCAASGSIFSTKTMGWYRQAPGKQREWVSLITTGLSTQ
YAESVKGRFTISRDNAKNTLYLQMSSLRAEDTAVYYCNVVPGRGATYWGQGTLVTV
KP (SEQ ID NO: 68)

TABLE 2-continued

OprI Binding Protein Sequences hzOprIv3 (also referred to herein as "OprI-7v3")
EVQLLESGGGEVQPGGSLRLSCAASGSIFSTKTMGWYRQAPGKGLEWVSLITTGLSTQ
YAESVKGRFTISRDNAKNTLYLQMSSLRAEDTAVYYCNVVPGRGATYWGQGTLVTV
KP (SEQ ID NO: 69)

hzOprI-7v4 (also referred to herein as "OprI-7v4")
EVQLLESGGGEVQPGGSLRLSCAASGSIFSTKTMGWYRQAPGKGLEWVSLITTGLSTQ
YAESVKGRFTISRDNAKNTVYL QMSSLRAEDTAVYYCNVVPGRGATYWGQGTLVTV
KP (SEQ ID NO: 70)

hzOprI-7v5
EVQLLESGGGEVQPGGSLRLSCAASGSIFSTKTMGWYRQAPGKGREWVSLITTGLSTQ
YAESVKGRFTISRDNAKNTLYLQMSSLRAEDTAVYYCNVVPGRGATYWGQGTLVTV
KP (SEQ ID NO: 88)

What is claimed is:

1. An isolated polypeptide comprising a first VHH domain that binds PcrV from *Pseudomonas aeruginosa*, wherein the first VHH domain comprises the CDRs of SEQ ID NO: 41 as determined by Chothia numbering.

2. The isolated polypeptide of claim 1, wherein the first VHH domain is humanized.

3. The isolated polypeptide of claim 1, wherein polypeptide comprises an immunoglobulin Fc region polypeptide.

4. The isolated polypeptide of claim 3, wherein the immunoglobulin Fc region polypeptide comprises the amino acid sequence of SEQ ID NO: 1, 2, 3, or 4.

5. The isolated polypeptide of claim 1, wherein the polypeptide comprises a second VHH domain that binds OprI from *Pseudomonas aeruginosa*.

6. The isolated polypeptide of claim 1, wherein the second VHH domain comprises the CDRs of SEQ ID NO: 62 as determined by Chothia numbering.

7. The isolated polypeptide of claim 6, wherein the first VHH domain and the second VHH domain are humanized.

8. The isolated polypeptide of claim 6, wherein the polypeptide comprises an immunoglobulin Fc region polypeptide.

9. The isolated polypeptide of claim 8, wherein the immunoglobulin Fc region polypeptide comprises the amino acid sequence of SEQ ID NO: 1, 2, 3, or 4.

10. The isolated polypeptide of claim 6, wherein the polypeptide comprises a third VHH domain that binds PcrV from *Pseudomonas aeruginosa*, wherein the first VHH domain and the third VHH domain bind different epitopes of PcrV.

11. The isolated polypeptide of claim 10, wherein the polypeptide comprises an immunoglobulin Fc region polypeptide.

12. The isolated polypeptide of claim 11, wherein the immunoglobulin Fc region polypeptide comprises the amino acid sequence of SEQ ID NOs: 1, 2, 3, or 4.

13. An isolated polypeptide comprising a first VHH domain that binds OprI from *Pseudomonas aeruginosa*, wherein the first VHH domain comprises the CDRs of SEQ ID NO: 62 as determined by Chothia numbering.

14. The isolated polypeptide of claim 13, wherein the first VHH domain is humanized.

15. The isolated polypeptide of claim 13, wherein the polypeptide comprises an immunoglobulin Fc region polypeptide.

16. The isolated polypeptide of claim 15, wherein the immunoglobulin Fc region polypeptide comprises the amino acid sequence of SEQ ID NOs: 1, 2, 3, or 4.

17. The isolated polypeptide of claim 13, wherein the polypeptide comprises a second VHH domain that binds PcrV from *Pseudomonas aeruginosa*.

18. The isolated polypeptide of claim 17, wherein the polypeptide comprises an immunoglobulin Fc region polypeptide.

19. The isolated polypeptide of claim 18, wherein the immunoglobulin Fc region polypeptide comprises the amino acid sequence of SEQ ID NO: 1, 2, 3, or 4.

* * * * *

UNITED STATES PATENT AND TRADEMARK OFFICE
CERTIFICATE OF CORRECTION

PATENT NO. : 10,344,078 B2
APPLICATION NO. : 15/144470
DATED : July 9, 2019
INVENTOR(S) : Andrew Hollands et al.

Page 1 of 1

It is certified that error appears in the above-identified patent and that said Letters Patent is hereby corrected as shown below:

In the Claims

Claim 6 Column 103, Line 60, "claim 1" should be changed to --claim 5--.

Signed and Sealed this
First Day of October, 2019

Andrei Iancu
*Director of the United States Patent and Trademark Office*